(12) United States Patent
Domingues et al.

(10) Patent No.: US 7,112,660 B1
(45) Date of Patent: Sep. 26, 2006

(54) MODIFIED CYTOKINE

(75) Inventors: Helena Domingues, Heidelberg (DE); Hartmut Oschkinat, Berlin (DE); Luis Serrano, Heidelberg (DE); Joerg Peters, Elberfeld (DE)

(73) Assignees: European Molecular Biology Laboratory, Heidelberg (DE); Bayer AG, Leverkusen (DE)

( * ) Notice: Subject to any disclaimer, the term of this patent is extended or adjusted under 35 U.S.C. 154(b) by 0 days.

(21) Appl. No.: 09/979,916

(22) PCT Filed: May 23, 2000

(86) PCT No.: PCT/IB00/00769

§ 371 (c)(1),
(2), (4) Date: Apr. 11, 2002

(87) PCT Pub. No.: WO00/73460

PCT Pub. Date: Dec. 7, 2000

(30) Foreign Application Priority Data

May 26, 1999 (GB) .................................. 9912350.7

(51) Int. Cl.
*C07K 14/00* (2006.01)
*A61K 45/00* (2006.01)

(52) U.S. Cl. ..................................... 530/351; 424/85.2

(58) Field of Classification Search ............... 424/85.2; 435/4, 69.52
See application file for complete search history.

(56) References Cited

U.S. PATENT DOCUMENTS 5,596,072 A * 1/1997 Culpepper et al. .......... 530/351

OTHER PUBLICATIONS

Wang et al., Proc. Natl. Acad. Sci. USA, 94:1657-1662, 1997.*
Wells, J.A. Biochemistry. 29(37):8509-8517, 1990.*
Bowie et. al., Science 247: 1306-1310, 1990.*

* cited by examiner

*Primary Examiner*—Eileen B. O'Hara
*Assistant Examiner*—Gyan Chandra
(74) *Attorney, Agent, or Firm*—Edwards Angell Palmer & Dodge LLP; David G. Conlin; John B. Alexander

(57) ABSTRACT

The invention relates to methods for the stabilisation of cytokines and to cytokines generated by such methods. The methods of the invention involve mutating the amino acid sequence of a cytokine so as to remove solvent-exposed hydrophobic residues, and/or mutating the amino acid sequence of the cytokine so as to stabilise one or more secondary structure elements in the molecule. These steps have the effect of destabilsing intermediates that are formed during the folding process, relative to the stability of the cytokine in its naturally folded state, so increasing the yield of the cytokine as produced in vitro.

4 Claims, 11 Drawing Sheets

Aggregated Protein

| Peptide | % helix AGADIR | % helix Experim. |
|---|---|---|
| wild type | 4 | 7 |
| mutant | 20 | 23 |

IL4Ch_wt: ATAQQFHRHKQLIRFLKRLDRNLWGLAG

IL4BCh  : ASAAEANRHKQLIRFLKRLDRNLWGLAG 15.0 kDa →

SEQUENCE LISTING

<160> NUMBER OF SEQ ID NOS: 12

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence : IL-4
      mutated sequence
<220> FEATURE:
<221> NAME/KEY: Interleukin-4 mutant
<222> LOCATION: (69)....(74)
<223> OTHER INFORMATION: IL-4 modified cytokine

<400> SEQUENCE: 1

Ser Ala Ala Glu Ala Asn
1               5

<210> SEQ ID NO 2
<211> LENGTH: 6
<212> TYPE: PRT
<213> ORGANISM: Homo sapiens

<400> SEQUENCE: 2

Thr Ala Gln Gln Phe His
1               5

<210> SEQ ID NO 3
<211> LENGTH: 28
<212> TYPE: PRT
<213> ORGANISM: Homo sapiens wild type IL-4 cytokine helix C sequence

<400> SEQUENCE: 3

Ala Thr Ala Gln Gln Phe His Arg His Lys Gln Leu Ile Arg Phe Leu
1               5                   10                  15

Lys Arg Leu Asp Arg Asn Leu Trp Gly Leu Ala Gly
            20                  25

<210> SEQ ID NO 4
<211> LENGTH: 28
<212> TYPE: PRT
<213> ORGANISM: modified Homo sapiens IL-4 cytokine helix C sequence

<400> SEQUENCE: 4

Ala Ser Ala Ala Glu Ala Asn Arg His Lys Gln Leu Ile Arg Phe Leu
1               5                   10                  15

Lys Arg Leu Asp Arg Asn Leu Trp Gly Leu Ala Gly
            20                  25

<210> SEQ ID NO 5
<211> LENGTH: 30
<212> TYPE: DNA
<213> ORGANISM: Homo sapien 5' PCR primer oligonucleotide

<400> SEQUENCE: 5
ctggagactg ccatggatca caagtgcgat                                    30

<210> SEQ ID NO 6
<211> LENGTH: 25
<212> TYPE: DNA
<213> ORGANISM: Homo sapien 3' PCR primer oligonucleotide

<400> SEQUENCE: 6

-continued

```
acgcggatcc ttatcagctc gaaca                                             25

<210> SEQ ID NO 7
<211> LENGTH: 33
<212> TYPE: DNA
<213> ORGANISM: Homo sapien PCR primer oligonucleotide

<400> SEQUENCE: 7
cagagcagaa gactagttgc accgagttga ccg                                    33

<210> SEQ ID NO 8
<211> LENGTH: 33
<212> TYPE: DNA
<213> ORGANISM: Homo sapien PCR primer oligonucleotide

<400> SEQUENCE: 8
cggtcaactc ggtgcaacta gtcttctgct ctg                                    33

<210> SEQ ID NO 9
<211> LENGTH: 27
<212> TYPE: DNA
<213> ORGANISM: Homo sapien PCR primer oligonucleotide

<400> SEQUENCE: 9
aggaacctca gtggcctggc gggcttg                                           27

<210> SEQ ID NO 10
<211> LENGTH: 27
<212> TYPE: DNA
<213> ORGANISM: Homo sapien PCR primer oligonucleotide

<400> SEQUENCE: 10
caagcccgcc aggccactga ggttcct                                           27

<210> SEQ ID NO 11
<211> LENGTH: 37
<212> TYPE: DNA
<213> ORGANISM: Homo sapien PCR primer oligonucleotide

<400> SEQUENCE: 11
ctgggtgcga gtgcagcaga agcaaacagg cacaagc                                37

<210> SEQ ID NO 12
<211> LENGTH: 37
<212> TYPE: DNA
<213> ORGANISM: Homo sapien PCR primer oligonucleotide

<400> SEQUENCE: 12
gcttgtgcct gtttgcttct gctgcactcg cacccag                                37
```

MODIFIED CYTOKINE

CROSS-REFERENCE TO RELATED APPLICATION(S)

This application is a §371 application of PCT /IP00/00769, filed May 23, 2000, which application is incorporated herein by reference.

The invention relates to methods for the stabilisation of cytokines and to cytokines generated by such methods. In particular, the methods of the invention include steps that destabilise intermediates that are formed during the folding of the cytokine, relative to the stability of the cytokine in its naturally folded state. This has the effect of increasing the yield of the cytokine as produced in vitro.

Cytokines are small proteins of between around 8 and 80 kDa that have a central role in both positive and negative regulation of immune reactions, as well as in integrating these reactions with other physiological compartments such as the endocrine and hemopoietic systems.

Well over one hundred different human cytokines have now been identified, that possess a wide variety of different functions. These molecules act by binding to specific receptors at the cell membrane, so initiating a signalling cascade that leads to the induction, enhancement or inhibition of a number of cytokine-regulated genes. There are various different types of cytokines, including the interleukins, interferons, colony stimulating factors, tumour necrosis factors, growth factors and chemokines. These cytokines function together in a complex network in which the production of one cytokine generally influences the production of, or response to, several other cytokines.

Clinically, cytokines have important roles in several areas of medicine, including their use as anti-inflammatories, and as agents used to treat a number of cancers, including non-Hodgkin's lymphoma, multiple myeloma, melanoma and ovarian cancer. Cytokines also have applications in the treatment of HIV, multiple sclerosis, asthma and allergic diseases.

The activity of cytokines can be inhibited by preventing the interaction of the specific cytokine with its receptor system, thereby suppressing the intracellular signals that are responsible for the cytokine's biological effects. The strategies that are available to block cytokine-receptor interactions generally involve the use of monoclonal antibodies against the cytokine or against its receptor. In addition, soluble receptors and cytokine receptor antagonists may be used (see Finkelman et al 1993; Rose-John Heinrich, 1994). Receptor antagonists are mutants of the wild type cytokine that are able to bind to cytokine receptors with high affinity, but which are not able to induce signal transduction and therefore do not generate a biological response. In the case of IL-4, two efficient antagonists have been reported in the literature that bind to the IL-4 receptor alpha with a $K_d$ similar to that of the wild type protein, but which are unable to recruit a second receptor component.

However, the therapeutic potential of soluble receptors and monoclonal antibodies has been shown to be rather limited, due to the high doses that are required, and the possible immunogenicity of these proteins (Finkelman et al 1993: Maliszewski et al 1994).

For these reasons, a great deal of attention has been devoted to the possible utilisation of cytokine-derived antagonists as therapeutic molecules. This new generation of bio-pharmaceuticals is expected to be of lower toxicity as compared to other substances (Buckel, 1996).

There are several practical reasons why there is an interest in optimising the production of cytokines (and cytokine antagonists) in bacteria such as E. coli. Although several eukaryotic expression systems, including insect, fungal, yeast and mammalian cell lines have been developed over recent years, the relative simplicity of bacteria makes these organisms advantageous hosts in most cases. E. coli, for example, has a fast growth rate (typical doubling time of 20 minutes), it is easy to manipulate and to screen for protein expression and for mutations, and it grows in a relatively cheap medium. As a result of these advantages, most protein drugs that are presently available on the market are produced by the large scale fermentation of E. coli carrying the gene of interest (Steven et al 1998). Although these high cell density culture systems are rather well established for E. coli, very little is known about their efficiency and viability with other host organisms.

Disadvantages related to the utilisation of E. coli and other prokaryotic expression systems in general include the tendency of this organism to produce heterologous protein in inclusion bodies, the absence of post-translational modifications, inefficient translation of human mRNA by the bacterial ribozymes, a characteristic codon usage and the inability to form disulphide bonds in the cytoplasm. These facts condition the folding and stability of the expressed protein and may cause aggregation.

Factors influencing the formation of inclusion bodies in E. coli include the cell growth temperature, co-expression with chaperones, the use of fusion proteins, secreting the protein into the periplasm, the use of different expression strains and expressing the protein including its pro-sequence. However, manipulation of these methods are only partially effective, if at all, in resolving this problem.

It should be noted that the formation of inclusion bodies is by no means an aberrant phenomenon that is limited to E. coli. It has also been reported for eukaryotic expression systems, like Saccharomyces cerevisiae and even for mammalian cells, both with inherent and heterologous proteins (Bowden and Georgiou, 1990).

An obligatory step in the recovery of a protein from inclusion bodies involves the use of denaturing, chaotropic agents such as urea or GudmHCl (guanidinium chloride) detergents or extremes of pH, to desolubilise the aggregates. Unfortunately, renaturation protocols are seldom simple and purifying a protein from inclusion bodies in a reasonable yield generally represents a significant challenge. Often, the protein of interest precipitates during refolding or may undergo irreversible chemical modifications due the presence of the denaturant.

When devising a strategy for the commercial production of a protein, it must be kept in mind that the conditions found in small scale growth tests should also be effective when the process is scaled-up to large scale fermentations. For example, the fact that co-overexpression of a given target with chaperones increases its solubility in a 1 litre shake-flask does not guarantee that the same will be observed during a 100,000 litre fermentation. It is therefore desirable to find simple solutions to the complex inclusion body problem.

In the case of disulphide-bonded proteins such as cytokines, it has been demonstrated that the conversion of reduced to oxidised protein proceeds through a series of intermediate species characterised by non-native intramolecular disulphide bridges (Creighton, 1997; De Felippis et al., 1993; Youngman et al., 1995). Various agents are available for the catalysis of the formation and reshuffling of disulphide bonds to their native pairing, although optimal conditions for complete, correct oxidative refolding can seldom be found. Therefore, during the in vitro folding of most disulphide containing proteins such as cytokines, a series of isoforms are obtained. Some of these isoforms precipitate and the native isoform, which is often a minor species, must be separated from all the others by HPLC. Frequently, although the protein accumulated in inclusion bodies seems sufficient to obtain the desired quantity of pure protein, the incurred loss during the preparation of the inclusion bodies and the refolding of the protein is so large, that only an insignificant amount of active protein may be recovered.

The therapeutic potential of cytokine-derived antagonists is thus diminished by virtue of the fact that these proteins are difficult to produce in large amounts in a cost-effective way. This is because they tend to form inclusion bodies when overexpressed in *E. coli.* and they refold in vitro in very low yields.

Therefore, it is of crucial importance to devise strategies that allow a more efficient production of cytokine antagonists, and alternative ways to block the interaction between cytokines and their receptors. Ideally, it would be desirable to design small molecules that were able to compete with cytokine for binding to its receptor.

The aim of the present invention is thus to design mutant cytokines that may be produced either as soluble proteins in bacteria or as proteins that will fold efficiently in vitro. Such a strategy would make the industrial production of cytokine antagonists more affordable and less laborious.

SUMMARY OF THE INVENTION

According to the present invention there is provided a method of stabilising a cytokine comprising one or both of the following steps:
a) mutating the amino acid sequence of the cytokine so as to remove solvent-exposed hydrophobic residues; and
b) mutating the amino acid sequence of the cytokine so as to stabilise one or more secondary structure elements in the cytokine;

such that during folding of the cytokine, an intermediate formed during the folding of the cytokine is destabilised relative to the cytokine in its folded state. This has the effect of improving the in vitro folding yield of the cytokine.

The method of the invention has been shown to allow the stabilisation of cytokines such that they may be produced recombinantly at low cost and in large volume. This method thus paves the way for the inexpensive production of these molecules, bringing the use of these molecules into mainstream therapy for a number of important diseases.

Any cytokine may be stabilised according to the present invention, including interleukins, interferons, colony stimulating factors, tumour necrosis factors, growth factors and chemokines.

Preferred cytokines for stabilisation according to the invention are "four helix bundle" cytokines that belong to the haematopoietic or class 1 cytokine superfamily. The three-dimensional structure of these proteins consists of a four-helix bundle with an "up-up-down-down" topology, including three disulphide bridges.

Based on the length of the polypeptide chain and on structural features, two main subfamilies may be identified in this superfamily. In addition, the interferons are frequently considered to constitute a third subfamily of the four helix bundle cytokines.

Members of this super family include the human growth hormone (HGH), granulocyte Macrophage-Colony stimulating factor (GM-CSF), granulocyte Colony stimulating factor (G-CSF), leukaemia inhibitory factor (LIF), erythropoietin (EPO), IL-2, IL-3, IL-4, IL-5, IL-6, IL-7, IL-9, IL-13, ciliary neurotrophic factor (CNTF), oncostatin (OSM) and the interferons among others. Some of the known members of these three subfamilies that have structures similar to IL-4 are listed in Table 1 below.

A striking feature of the haematopoietic cytokine superfamily is that, despite their common form, the family members have little or no sequence homology. However, the fact that these proteins are all extracellular signalling molecules, that they share the same unique four helix bundle topology and a similar gene organisation, suggests that they are all related by a process of divergent evolution.

Four helix bundle cytokines bind to a class of receptors known as the hematopoietin receptor superfamily or type 1 cytokine receptor superfamily. These receptors comprise an extracellular cytokine binding domain which is highly homologous within the family, a single transmembrane domain, and an intracellular domain that lacks intrinsic tyrosine kinase activity. The extracellular domain has four conserved cysteines and a characteristic tryptophan-serine-X-tryptophan-serine (the so called tryptophan box) motif that is thought to be important for efficient receptor folding (for reviews see Bazan, 1990 and Gullberg et al 1995).

TABLE 1

Class 1 hematopoietic cytokine superfamily
Receptor binding within the hematopoeitic family

| Subclass | Examples with known structures | Putative Members |
| --- | --- | --- |
| Short chain | IL-2, IL-4, IL-5$^a$ GM-CSF, M-CSF$^a$ | IL-3, IL-7, IL-9 IL-13, IL-15 |
| Long chain | GH, LIF, G-CSF, IL-6 | OSM, IL-11, TPO IL-12, CNTF, PRL EPO |
| Interferon | IFN-$^\beta$ and IFN-$^\gamma$ | |

CNTF. ciliary neurotrophic factor: EPO. erythropoietin: OSM. oncostatin: TPO. thrombopoietin: LIF. Leukemia inhibitory factor: PRL. prolactin: IFN. interferon.
$^a$The protein is a non-covalent dimer: $^a$The protein is a disulfide linked dimer.
This table is a modified and updated version of that in (Mott et al., 1995)

The most extensively characterised cytokine-receptor system is that of the human growth hormone. A determination of the three dimensional structure of this protein bound to two chains of the same receptor (de Vos et al 1992) has laid the grounds for understanding the principles that are involved in molecular recognition and signal transduction by four helix bundle cytokines and their receptors. From the data that is available in the literature on other cytokine receptor systems, it is clear that the ligand induced receptor homo or hetero-oligomerisation is a general strategy that is used by members of the haematopoietic cytokine family.

In order to understand the invention fully, it is important to appreciate some of the principles that govern protein folding. Current theory in this area dictates that folding intermediates exist in the folding pathway for most naturally-occurring proteins. Some of these intermediates define the productive folding pathway to the native protein, while others represent off-pathway species that can form aggregates, directing the protein irreversibly to a non-native confirmation (see Baldwin, 1996). Some of these folding intermediates are stable, containing a significant amount of native-like secondary structure, although lacking the tertiary interactions that are characteristic of the native conformation. The native state only emerges upon "fine-tuning" of the specific interactions in these intermediates. In this light, the occurrence of aggregation is seen as a function of the solubility and stability properties of the folding intermediates with respect to the environment in which the folding reaction takes place.

It has become clear from work in which mutations have been introduced that have the effect of alleviating folding defects associated with temperature-sensitive substitutions, that it is possible to optimise folding pathways without altering the activity and stability of the mature protein. A detailed discussion of the literature relevant to the protein folding problem may be found in the Ph.D. thesis of Helena Domingues (1999 "Rational design strategies to improve cytokine foldability and minimisation of a functional motif: the IL-4 case" University of Utrecht, ISBN 90-393-2081-0).

From the background literature in this area, it follows that aggregation both in vitro and in vivo results mainly from the accumulation of folding intermediates that have a high tendency to associate (Fink, A. L. 1998) and establish non-native interactions that direct proteins to inactive conformations (Booth et al. 1997). The folding of a protein to a unique 3D structure is depicted in FIG. 1. Folding intermediates can accumulate because there is a high energy barrier between them and the transition state, and/or because the energy barrier between the folded and the transition state is low. In the first case shown in this figure, folding is slow and the concentration of folding intermediates is high. In the second case, the folded state unfolds frequently under physiological conditions and, as a result, a significant concentration of folding intermediates can be present. Therefore, the relative destabilisation of folding intermediates and/or the stabilisation of the folded state, with respect to the folding transition state could help protein fold more efficiently (Munoz et al 1994a).

The invention relates to methods that incorporate the engineering of amino acid substitutions that selectively destabilise any appreciative intermediate in the folding pathway for cytokines. The mutants thus obtained either remain soluble during expression, and/or refold more efficiently in vitro. At the same time, these mutants are of similar activity to the wild type protein.

A first aspect of the method of the invention involves mutating the amino acid sequence of the cytokine so as to remove solvent-exposed hydrophobic residues. Amino acid substitutions made involve the substitution of hydrophobic residues (such as Valine, Leucine, Isoleucine, Phenylalanine, Tryptophan, Methionine, Proline) to more polar residues (such as Lysine, Arginine, Histidine, Aspartate, Asparagine, Glutamate, Glutamine, Serine, Threonine, Tyrosine).

This aspect of the method is based on the observation that folding intermediates are often characterised by the presence of a significant amount of secondary structure and ill-defined tertiary structure that are stabilised by hydrophobic interactions. Therefore, it appears plausible that hydrophobic residues that are exposed in the folded state (as a result of a tertiary fold) will be buried in a folding intermediate. Mutation of such residues to a more polar amino acid has the effect of destabilising the intermediate with respect to the folded state to the so-called inverse hydrophobic effect. A schematic representation of the inverse hydrophobic effect is shown in FIG. 2. The replacement of hydrophobic residues by more hydrophilic residues should destabilise both the denatured ensemble and the intermediate with respect to the native state. This will increase the folding rate and reduce kinetic aggregation processes that result from the accumulation of intermediates.

There are various methods available for the indentification of solvent-exposed residues, including the use of standard molecular graphics computer programs such as Ras-Mol, QUANTA™ (Molecular Simulations Inc., 9685 Scranton Road San Diego, Calif. 02121) and SYBYL™ (tripos Inc., 1699 South Hanley Rd., St. Louis, Mo., 63144, USA). Furthermore, it is not necessarily essential that the three-dimensional structure of a protein is known. A number of sophisticated computer programs and bioinformatics platforms are now becoming available that allow protein structure to be predicted with some accuracy from amino acid sequence alone. It ma also be possible to infer the position of solvent-exposed residues for a cytokine of unknown structure from a homologous orthologous or closely-related cytokine for which the structure is available, by using homology modeling or threading methods (see Jones D. T. 1997). When choosing residues to mutate in this step of the method, solvent-exposed hydrophobic residues should Ideally be chosen that are not conserved between the cytokine of interest and other homologous or closely-related cytokines.

For example, in the case of IL-4, tryptophan 23 and leucine 91 are solvent-exposed residues in the human sequence; in most of the other members of the IL-4 family, a serine residue (hydrophilic) is found at this position. Accordingly either one, or preferably both of these residues provide good choices for mutation. In this case, serine is an advisable choice as a replacement residue, since not only is this residue hydrophilic, but its presence at this position in closely related IL-4 proteins lends support for the inference that its presence at this point is probably not harmful to activity, and may even be advantageous.

The second aspect of the method involves mutating the amino acid sequence of the cytokine so as to stabilise one or more secondary structure elements in the cytokine. In a preferred aspect of this embodiment of the invention, helix-stabilising residues are introduced into the sequence of the protein. This element of the method is based on the observation that secondary structure elements are stabilised by a set of local interactions between neighbouring residues. By secondary structure elements is meant α helices and β sheets, loops and β-turns, preferably α helices.

Preferred alpha helix-promoting amino acid residues include Alanine, Asparagine, Cysteine, Glutamine, Glutamate, Leucine, Methionine, Phenylalanine, Tryptophan or Tyrosine. Helix-breaker residues that disrupt the structure, such as Proline and Glycine, should be avoided.

There are a number of available techniques to allow the rational design of proteins containing stabilised secondary structural elements. The principles that underlie the formation and stability of β sheet structures are only now beginning to emerge. However, in the case of alpha helices, these principles are quite well understood (see Chakrabartty and Baldwin 1995). This knowledge has arisen from studies with model synthetic peptides, and also from the analysis of the thermodynamic and kinetic properties of mutant proteins carrying amino acid substitutions in their alpha helices.

An important contribution has come from attempts to design de novo proteins with one or more segments of helical structure, the so-called helix bundle (see Kohn and Hodges 1998). More frequently than not, the designed proteins lack the specific tertiary interactions that are characteristic of folded proteins, but the helical segments are usually well defined.

The information gathered from these different types of studies has been used to develop and to optimise algorithms that can predict the helical content of peptides in aqueous solution. An algorithm termed AGADIR is one of these methods (Munoz et al, 1994 b,c,d; Munoz et al, 1997; Lacroix et al., 1998), and has proven to be a useful tool in the design of peptides with high content of helical structure.

In this element of the method, when identifying residues that can be mutated in order to increase the helical propensity of the constituent amino acid sequence, long range interactions between residues should ideally remain unaffected. The target residues should ideally be solvent-exposed, make only local contacts inside the alpha helix, and should not be involved in extensive interactions with the rest of the molecule.

The effect of improved local interactions on the folding kinetics and on the stability of a given protein will depend on the thermodynamic and structural characteristics of eventual intermediates in the folding pathway, as well as on those of the native and denatured state. If an element of the secondary structure is folded in the transition state but not in a folding intermediate, its stabilisation through the introduction of favourable native-like interactions should lower the energy barrier of the folding transition state, so accelerating the folding reaction (see FIG. 3). Favorable electrostatic pairs may also be introduced.

In selecting the appropriate helix to mutate in a cytokine, several criteria may be considered. Firstly, it is advantageous to choose a helix that is not conserved among closely related members of the cytokine family. Second, residues should be chosen that are not involved in binding to receptor, such as, for example, in the case of IL-4, residues at the N-terminus of helix C of the cytokine. Third, it may be advantageous to choose a helix that is flexible in the structure. However, this is not necessarily the case and often it is not known whether or not a given helix is flexible. If it is known that a given helix, or parts of it, are very flexible then, particularly when the flexible part does not correspond to a functional site, this site is obviously a good target for stabilisation by mutagenesis. This may be predicted from nuclear magnetic residence $^{15}$N relaxation and hydrogen exchange studies on the cytokine concerned.

In areas of the protein that have a low average helical content, mutations may be introduced that increase the average helical content of this region. These mutations include residues that are better helix formers than the residues that they replace (see Chakrabartty 1995; Muñoz and Serrano, 1994e). Mutations may also be introduced so as to allow the formation of favourable electrostatic pairs.

When designing a helix-forming amino acid substitution to incorporate into a cytokine to improve its stability, it should be borne in mind that if, in addition to being present in the naturally-folded protein, the α-helix is also present in the intermediate that causes the folding problem, then its stabilization will affect both the folded and the intermediate states to the same extent, and therefore no significant effect in refolding will be found, at least under low denaturant concentrations. At moderate or high denaturant concentrations, the intermediate will be destabilized with respect to the native state, and folding will proceed faster.

If the α-helix is not present in the intermediate but it is present in the transition state, its stabilization should result in a lower energy barrier between the intermediate and the transition state and consequently increase the folding rate. Therefore, under moderate denaturant concentrations, like those used in protein refolding experiments, the stabilization of α-helices will always accelerate the folding reaction, leading to a more productive folding process.

Helix C is considered by the inventors to be a preferred helix for stabilisation of cytokine according to the invention. Stabilisation of this helix is thought to act by preventing protein aggregation mediated by a folding intermediate, probably due to the acceleration of the folding reaction and a concomitant decrease in the concentration of a putative folding intermediate.

In the specific example of IL-4, helix C is not very conserved among the members of the IL-4 family. Furthermore, it is known that the first residues at the N-terminus are not involved in binding to the receptor (Wang et al., 1997), and Nuclear Magnetic Resonance $^{15}$N relaxation and hydrogen exchange studies on IL-4 have shown that this region of helix C is very flexible (Redfield et al., 1992; Redfield et al., 1994a; Redfield et al., 1994b). As additional support for these observations, the algorithm AGADIR1s-2 predicts a low average helical content (4%) for this helix.

Examples of helix stabilising mutations for IL-4 are the mutation of threonine 69 to serine; glutamine 71 to alanine; glutamine 72 to glutamate, phenylalanine 73 to alanine; histidine 74 to asparagine. The sequence SAAEAN may thus be introduced at positions 69–74 in the full IL-4 amino acid sequence, replacing TAQQFH.

In the case of mutating helix C of IL-4, at the same time as introducing amino acid residues that are better helix-formers, the N-capping box motif present in the wild type protein (T—X—X—Q) may be replaced by a better counterpart (S—X—X—E) whilst at the same time promoting the formation of a helix. In this embodiment of the invention, the wild type IL-4 helix sequence:

ATAQQFHRHKQLIRFLKRLDRNLWGLAG may be replaced by the sequence:

ASAAEANRHKQLIRFLKRLDRNLWGLAG; the residues in bold are those mutated.

The IL-4 functional receptor has been shown to be a heterodimer comprising a high affinity component, the IL-4Ralpha, and a low affinity subunit that might be either the IL-2 common gamma chain (Russel et al., 1993) or the IL-13Ralpha (Matthews et al., 1995), depending on the target cell. Data reported in Matthews et al., 1995 suggest that IL-4 may bind to a distinct receptor, called the type II IL-4 receptor, that is composed of the IL-4Rα chain and the low affinity binding receptor of IL-13 (IL-13Rα). These data explain why IL-2 and IL-13 can elicit biological responses similar to IL-4 on certain types of cells. In the specific case of IL-4, the inventors therefore consider it advantageous to mutate the cytokine so as to allow binding of the cytokine to IL-4Rα but to prevent binding of the cytokine to IL-13Rα and/or the $\gamma_c$ chain. The possibility to inhibit the two cytokines simultaneously may prove an efficient means to curb the symptoms that are associated with allergic diseases; for this reason these IL-4 antagonists are of high therapeutical interest.

It may also be advantageous to introduce mutations other than those intended to stabilise folding of the natural protein at the same time that mutagenesis according to the invention is performed. For example, two efficient antagonists of IL-4 have already been reported in the literature. These are IL-4Y124D (Y) (Kruse et al., 1992) and IL-4R121DY124D (RY) (Kruse et al., 1993; Tony et al., 1994). These IL-4 mutants bind IL-4Rα with a $K_d$ similar to that of the wild type protein, but are unable to recruit a second receptor component (Duschl et al., 1995). This results in the formation of an unproductive complex with IL-4Rα, which has no detectable biological activity. IL-4 antagonists have also been shown to inhibit IL-13 (Grunewald et al., 1998; Tony et al., 1994), because the receptor system of this cytokine requires IL-4Rα for signal transduction (Smerz-Bertling et al., 1995; Tony et al., 1994). In one aspect, the invention therefore relates to the substitution of an aspartate residue at position 121 and/or 124 in the full length IL-4 amino acid sequence.

The findings that are presented herein support the view that alpha helical sequences in proteins are not necessarily optimised for maximal protein stability. This poses no problems when proteins are being synthesised and are operating in their natural environment, where they have evolved to fulfil their biological role. However, the situation is different when proteins are synthesised are manipulated in a heterologous environment that may condition the stability of the native proteins and of other species in the folding pathway. In this case, improvements in the stability of alpha helices may increase both the stability of the native state and the speed of the folding reaction.

Furthermore, certain algorithms such as AGADIR, have been found to be excellent tools for the rational design of helical sequences that possess enhanced stability.

According to a further aspect of the invention, the method comprises a further step c) of including the pro-sequence of the cytokine at its N terminus. It is known that many proteins, including a variety of proteases, growth factors, polypeptide hormones, neuropeptides and plasma proteins, are synthesized in vivo in the form of pre-pro-proteins. The pre-sequence targets the protein for transport into the endoplasmic reticulum (ER) and for extracellular secretion. The pro-sequence is usually attached to the N-terminus, following the pre-sequence, but it can also be found at the C-terminus or a combination of both. A role for pro-sequences in protein folding has been suggested from studies with different proteases (for reviews see Shinde el al., 1993; Eder & Fersht, 1995).

The most extensively investigated cases of pro-sequence mediated folding are those of subtilisin (Eder el al., 1993), and α-lytic protease (Baker et al., 1992). In the absence of the propeptide these proteins fold into a stable partially-folded intermediate with characteristics of the molten-globule state, but which lacks enzymatic activity. Addition of the pro-sequence lowers the activation energy barrier of the folding reaction either by stabilizing the transition state for folding or by destabilizing the non-native intermediate, resulting in the formation of the native conformation (see FIG. 4).

According to a further aspect of the invention, the method comprises a further step d) of expressing the cytokine in the host cell in conjunction with a foldase and/or with a chaperone protein.

In recent years it became clear that protein folding in the cell is mediated by two different classes of accessory proteins, known as foldases and chaperones. Foldases catalyse steps such as the formation and isomerization of disulfide bridges, and the isomerization of peptide bonds preceding proline residues. In a number of studies, the co-expression of foldases has been found to enhance the folding of proteins secreted into the periplasm of *E. coli* (for a review see Georgiou & Valax 1996; Hockney, 1994).

The two most extensively characterized families of chaperones are the Hsp70, which includes DnaK and its helper proteins, DnaJ and GrpE, and the Hsp60. The latter is also known as the chaperonin family, and comprises the bacterial GroEL/GroES system, and several analogues found in mitochondria and chloroplasts (for a review Hartl et al., 1994; Martin & Hartl, 1994). The GroEL/GroES system has been heavily investigated both structurally (Braig et al., 1994; Mande el al., 1996) and mechanistically (Corrales & Fersht, 1996). GroEL is composed of two heptameric rings on top of each other forming a double-doughnut with a lid on top of it (GroES). Experimental evidence points to a model for protein folding in the cytoplasm of *E. coli* in which Hsp70 and Hsp60 are sequentially involved (Langer et al., 1992). The members of the Hsp70 family bind proteins co-translationally, as they are being synthesized, and guide them through the first folding steps until a molten-globule-like state is attained. Exposed hydrophobic patches on the surface of these intermediates are then recognized by the GroEL/GroES system which keeps them in a folding-competent state. The folding of the polypeptide chain takes place inside the hollow structure of GroEL and the protein is released upon ATP hydrolysis. If one cycle is not enough for proper folding, the procedure will be repeated until a correctly folded state is achieved (Heyrovska et al., 1998).

In order to carry out chaperone-assisted protein expression, bacteria should be transformed with two distinct plasmids, one containing the gene coding for the protein of interest and the other the gene coding for the chaperone. The plasmids should have different replication origins, so that they can be stably maintained in the same bacterial cell. Furthermore, they should carry different antibiotic resistance markers, in order to allow selection for the simultaneous presence of both plasmids. The promoters are usually the same for the two plasmids, so that expression of the target protein and the chaperonin can be induced concomitantly. It some cases, it might be useful to use different promoters so that the chaperonin can be induced earlier. The expression of the target protein is then induced at a later stage, when the levels of chaperonin are already high enough to mediate folding efficiently (Cole, 1996).

There are several well documented cases in the literature in which the co-expression of the GroEL/GroES or the DnaK/J operon has been reported to increase the amount of soluble protein. Dihydrofolate reductase (DHFR) is one of the proteins which is produced as inclusion bodies in the absence of GroEL/S. When this chaperonin system is co-expressed with the protein, the amount of protein present in the soluble fraction increases drastically, allowing the purification of 3–5 mg of active enzyme per litre of bacterial culture (Dale et al., 1994). A similar effect has been observed for the co-expression of GroEL/S or DnaK with several tyrosine kinases (Amrein et al., 1995). The co-production of DnaK has also been shown to improved the solubility of hG-CSF (Pérez-Pérez et al., 1995) and hGH (Blum el al., 1992), two cytokines of the IL-4 family.

Preferably, the chaperonin used in step d) is the GroEL/ES system or thioredoxin. However, there is no general rule as to which chaperone to choose in order to improve the in vivo folding properties of a given protein. The chaperone that is able to bind an aggregation-prone intermediate will be the most adequate one, but only by doing the experiment can this answer be found. Furthermore, for some proteins, the expression of the chaperone is not sufficient to obtain soluble protein, and an approach combining several of the factors discussed above may be more suitable. With the catalytic subunit of bovine pyruvate dehydrogenase phosphatase it has been found necessary to lower the growth temperature to 30° C. in order to obtain soluble active protein (Lawson et al., 1993). Another factor that should be taken into consideration is that the co-expression with chaperones may decrease the expression levels of the target protein. This effect probably arises from a competition between the chaperone and the protein for components needed for protein synthesis like ribosomes, amino acids or t-RNAs (Dale, et al., 1994). Furthermore, high levels of chaperone expression can be detrimental to *E. coli* (Blum et al., 1992) and very little is known about the behaviour of cells overexpressing chaperones in the fermentors used for the large-scale production of biopharmaceuticals (Georgiou & Valax, 1996).

According to a further aspect of the invention, there is provided a mutant cytokine, or fragment thereof, generated by a method according to any one of the aspects of the invention that are described above, and functionally equivalent variants thereof. Such a cytokine may be an interleukin, an interferon, a colony stimulating factor, a tumour necrosis factor, a growth factor or a chemokine. Preferably, a cytokine stabilised according to the invention is a "four helix bundle" cytokine, such as those belonging to the haematopoietic or class 1 cytokine superfamily, including HGH, GM-CSF, G-CFC, LIF, EPO, IL-2, IL-4, IL-5 and IL-6. Due to the increased commercial value of drugs for mammals, cytokines that are derived from mammals, particularly humans, are preferred targets for stabilisation according to the present invention.

By the term "functionally-equivalent" is meant that the mutant cytokines proteins retain one or more of the biological functions possessed by the wild type cytokine. In the case of IL-4, such functions include functions such as control of the growth and differentiation of immune cells, defence against helminthic macroparasites, the rejection of certain tumours and the specific induction of IgE antibodies. Biological functions of other cytokines will be clear to those of skill in the art. The term "variants" includes, for example, mutants containing amino acid substitutions, insertions or deletions from the wild type cytokine sequence, as well as natural biological variants (e.g. allelic variants or geographical variations within the species from which the cytokine molecule is derived). Variants with improved function from that of the wild type sequence may be designed through the systematic or directed mutation of specific residues in the protein sequence. This term also refers to molecules that are structurally similar to the wild type cytokine, or that contain similar or identical tertiary structure.

Derivatives of the molecules, variants and functional equivalents described above are also included as embodiments of this aspect of the invention. Such derivatives may include one or more additional peptides or polypeptides fused at the amino- or carboxy-terminus of the modified cytokines. The purpose of the additional peptide or polypeptide may be to aid detection, expression, separation or purification of the protein or it may lend the protein additional properties as desired. Examples of potential fusion partners include beta-galactosidase, glutathione-S-transferase, luciferase, a polyhistidine tag, a T7 polymerase fragment, a secretion signal peptide or another cytokine or cytokine receptor. Such derivatives may be prepared by fusing the peptides either genetically or chemically.

Preferably, the mutant cytokines produced by the method of the present invention show an increase in refolding yield of at least two-fold, preferably five-fold or more, or more preferably ten-fold or more.

In one preferred embodiment of the invention, the cytokine is IL-4 or a derivative thereof, IL-4 is a very important immunoregulatory cytokine that controls the growth and differentiation of various types of immune cells, and which is involved in defence against helminthic macroparasites, and in the rejection of certain tumours. Perhaps the most important clinical role of IL-4 is the specific induction of IgE antibodies that are responsible for the development of the symptoms that are typically associated with allergic reactions. It is now evident that IL-4 plays a dominant role in the allergic response, as this protein determines whether B-cells give rise to IgE or to other types of antibodies. Consequently, drugs that are able to interfere with the activity of IL-4 will help reduce IgE levels and will render allergic reactions amenable to pharmaceutical control. A pre-requisite to the design of such drugs is the detailed understanding of the principles that govern the binding of IL-4 to its receptor system. Human IL-4 mutated at position 23, at position 91 or at both positions 23 and 91 in the full length sequence, and functionally equivalent fragments or variants thereof form a particularly preferred aspect of the invention. Advantageously, any mutation introduced at these positions may be a serine residue. Alternatively, or additionally, the IL-4 protein may contain one or more of the following mutations: threonine 69 to serine; glutamine 71 to alanine; glutamine 72 to glutamate, phenylalanine 73 to alanine; histidine 74 to asparagine. The sequence SAAEAN may thus be introduced at positions 69–74 in the full IL-4 amino acid sequence, replacing TAQQFH.

According to a still further aspect of the invention, there is provided human IL-4 including at positions 68–95 in the full length amino acid sequence, the sequence ASAAEANRHKQLIRFLKRLDRNLWGLAG, and functionally equivalent fragments or variants thereof.

The IL-4 proteins and derivatives thereof generated by the method of the invention may be used for the purification of Il-4Ralpha. Accordingly, the invention provides a method for the preparation of IL-4Ralpha protein comprising passing a composition containing IL-4Ralpha through an affinity column to which a mutant IL-4 protein is bound, washing the column, and eluting IL-4Ralpha from the column. Preferably, the mutant IL-4 protein is mutated at position 23, at position 91 or at both positions 23 and 91 in the full length sequence, most preferably mutated to serine at either or both of these positions. Alternatively, or additionally, the IL-4 protein may contain one or more of the following mutations: threonine 69 to serine; glutamine 71 to alanine; glutamine 72 to glutamate, phenylalanine 73 to alanine; histidine 74 to asparagine.

Presently, IL-4Ralpha is purified by affinity chromatography on extremely expensive purification columns that are packed with IL-4WT. The stabilized mutant IL-4 proteins produced by the methods described above will be much less expensive to produce in large quantities and will therefore allow purification columns to be produced at a lower cost, so diminishing the cost of preparing IL-4Ralpha protein for therapeutic use.

According to a still further aspect of the present invention, there is provided the use of a cytokine mutated according to any one of the aspects of the invention described above to produce antibodies against the cytokine. In particular, a mutant IL-4 protein as described above may be used in this aspect of the invention. Antibodies generated by this method have important uses as diagnostic and therapeutic tools.

According to a still further aspect of the invention there is provided a peptide comprising a fragment of a mutant cytokine as described above, or a functional equivalent thereof.

Such peptides may be derived from wild type cytokines or they may be prepared synthetically or using techniques of genetic engineering. In particular, synthetic molecules that are designed to mimic the tertiary structure or active site of a cytokine are considered advantageous. Although peptides are not ideal therapeutic drugs, the fact that they can be readily obtained by chemical synthesis methods allows the incorporation of unnatural amino acids, modified peptide bonds, or chemical groups that may increase the intrinsic stability of the peptides and their resistance to proteolytic degradation. Furthermore, active peptides can be used as lead compounds that can be further optimized through combinatorial screening, and may be emulated by small organic frameworks that offer the biostability and bioavailability required for therapeutic drugs (see Emmos et al., 1997).

An important question is how to find the best possible peptide candidate that is able to mediate the desired biological effect in the most efficient way. Molecular dynamic (MD) simulations provide one method that can assist rational design in selecting the most promising candidates in terms of foldability (see Cregut et al., 1999) Therefore, it is often convenient to combine rational strategies with irrational approaches in which the best peptide ligands are selected by screening libraries of compounds with diverse functional characteristics. Phage display technology has been of assistance in the creation and screening of vast peptide libraries (Cwirla et al., 1990; Smith et al., 1985). This methodology has been successfully used to isolate peptide mimetics of erythropoietin (EPO) (Wrighton et al., 1996). One of these peptides is able to bind the EPO receptor with an apparent $K_d$ of 0.2 µM, and the three-dimensional structure of this peptide in complex with the EPO receptor has also been determined (Livnah el al., 1996). The small peptide (20 residues) dimerizes forming a four-stranded anti-parallel β-sheet that is able to bind two EPO receptor molecules, and it has been shown to stimulate cell proliferation in vivo and erythropoiesis in mice (Wrighton el al., 1996).

The main disadvantage of screening methods is the long time necessary to pan the libraries for binding to the target. Then, it is necessary to characterize the best hit and start another time-consuming round of selection. It is, therefore, important to devise rational strategies that integrate structural and mutagenesis data. Molecular mimics designed in this way are likely to provide reliable starting points with affinities comparable to those found in the first rounds of combinatorial screening studies (typically in the high µM range). An approach combining phage display and rational design has been used previously to improve the stability and affinity of a two-helix derivative of the three-helix Z-domain of protein A. This 59 residue three-helix bundle binds the Fc portion of immunoglobulin G (IgG) with a $K_d$ of 10 nM. The binding domain has been reduced to a 33 residue peptide that is able to bind IgG with virtually the same affinity as the wild-type protein (Braisted et al., 1996).

According to a further aspect of the invention there is provided a nucleic acid molecule encoding a mutant cytokine or a peptide according to any one of the aspects of the invention described above. The invention also includes methods for the production of cytokines and peptides as described above, comprising introducing a nucleic acid encoding the cytokine or peptide into a host cell, such as an E. coli bacterium.

According to a still further aspect of the invention, there is provided a mutant cytokine or peptide according to any one of the above-described aspects of the invention, for use as a pharmaceutical. A further aspect of the invention provides for the use of such cytokines or peptides in the manufacture of a medicament for the treatment or prevention of a disease in a mammal, preferably a human. Advantageously, the disease may be an allergy-related condition. The invention also provides a method of preventing or treating an allergy comprising administering to a patient a mutant cytokine or peptide as described above.

According to a still further aspect of the invention, there is provided a pharmaceutical composition comprising a mutant cytokine or peptide according to any one of the above-described aspects of the invention, optionally as a pharmaceutically-acceptable salt, in combination with a pharmaceutically-acceptable carrier. The invention also provides a process for preparing such a pharmaceutical composition, in which such a mutant cytokine or peptide is brought into association with a pharmaceutically-acceptable carrier.

According to a still further aspect of the invention, there is provided a diagnostic kit comprising a mutant cytokine or peptide according to any one of the above-described aspects of the invention.

The invention also provides a transgenic non-human mammal, carrying a transgene encoding a mutant cytokine or peptide according to any one of the above-described aspects of the invention. A further aspect of the invention provides a process for producing such a transgenic animal, comprising the step of introducing a nucleic acid molecule encoding the mutant cytokine or peptide into an embryo of a non-human mammal, preferably a mouse.

Various aspects and embodiments of the present invention will now be described in more detail by way of example, with particular reference to methods for the stabilisation of IL-4. It will be appreciated that modification of detail may be made without departing from the scope of the invention.

EXAMPLE 1

Figure 1:
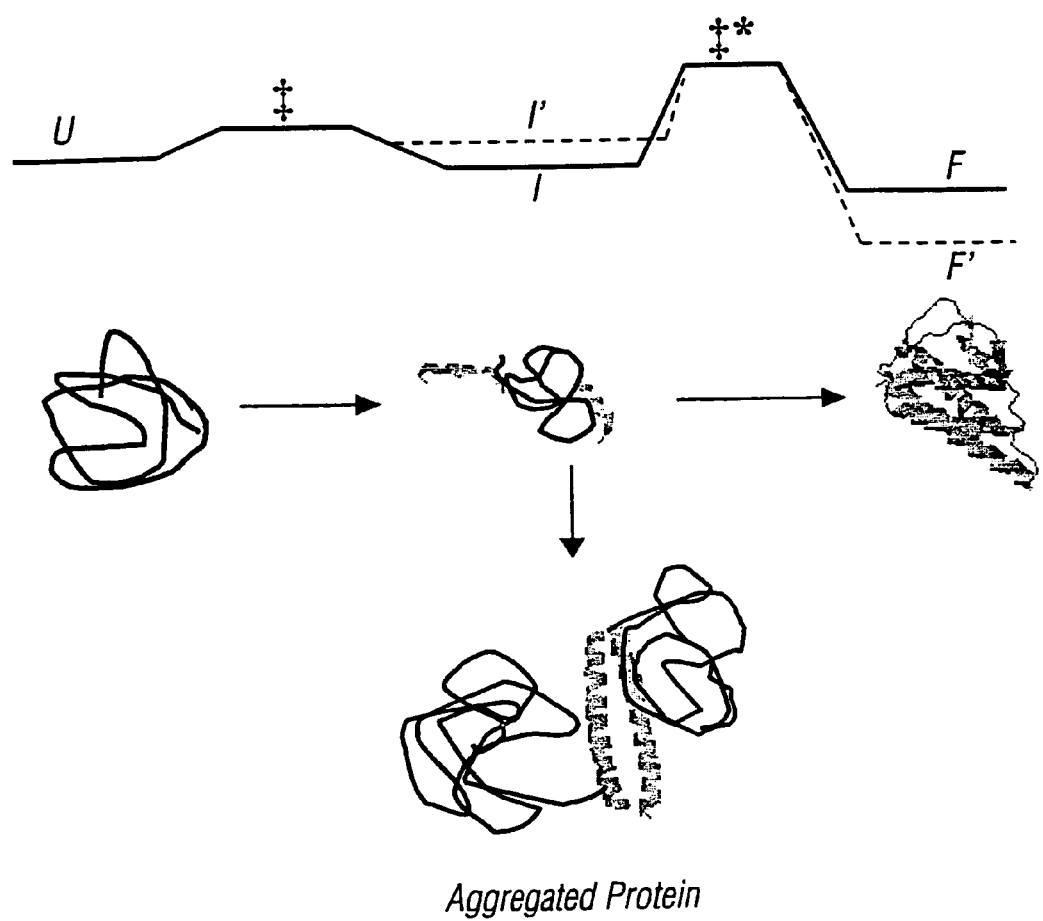
FIG. 1: Schematic representation of the folding of a protein to a unique three-dimensional structure (folded state—F) from a linear sequence of amino acids (the unfolded state—U). This is a complex process that usually involves the formation of stable folding intermediates (I) that are separated by an energy barrier (‡) from the unfolded and folded state. These intermediates can accumulate to high concentration during the folding reaction leading to protein aggregation. The accumulation of intermediates may be due to a high energy barrier between the intermediate and the transition state for folding (‡*) or a low energy barrier between the folded state and the transition state. Therefore, the selective destabilization of folding intermediates (I') and/or the stabilization of the folded state (F') can help proteins fold more efficiently.
Figure 2:
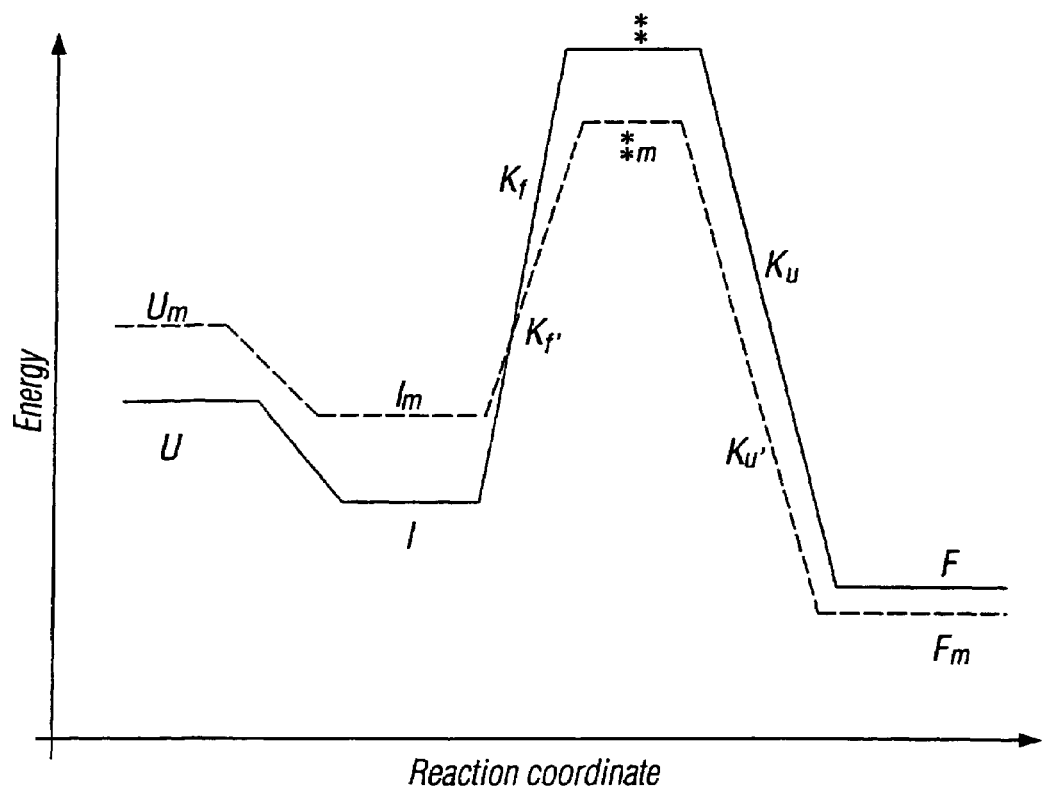
FIG. 2: Schematic representation of the inverse hydrophobic effect. U and $U_m$ represent the unfolded conformational ensemble, in the wild type protein and in the mutant, I and F, $I_m$, and $F_m$, represent, respectively, the intermediate and the folded state in the wild type and the mutant, $K_u$ and $K_f$ are the unfolding and folding rate constants, and ‡ symbolizes the transition state. The replacement of hydrophobic residues by more hydrophilic ones should, in principle, destabilize both the denatured ensemble and the intermediate with respect to the native state. This will increase the folding rate and reduce kinetic aggregation processes resulting from the accumulation of intermediates.
Figure 3:
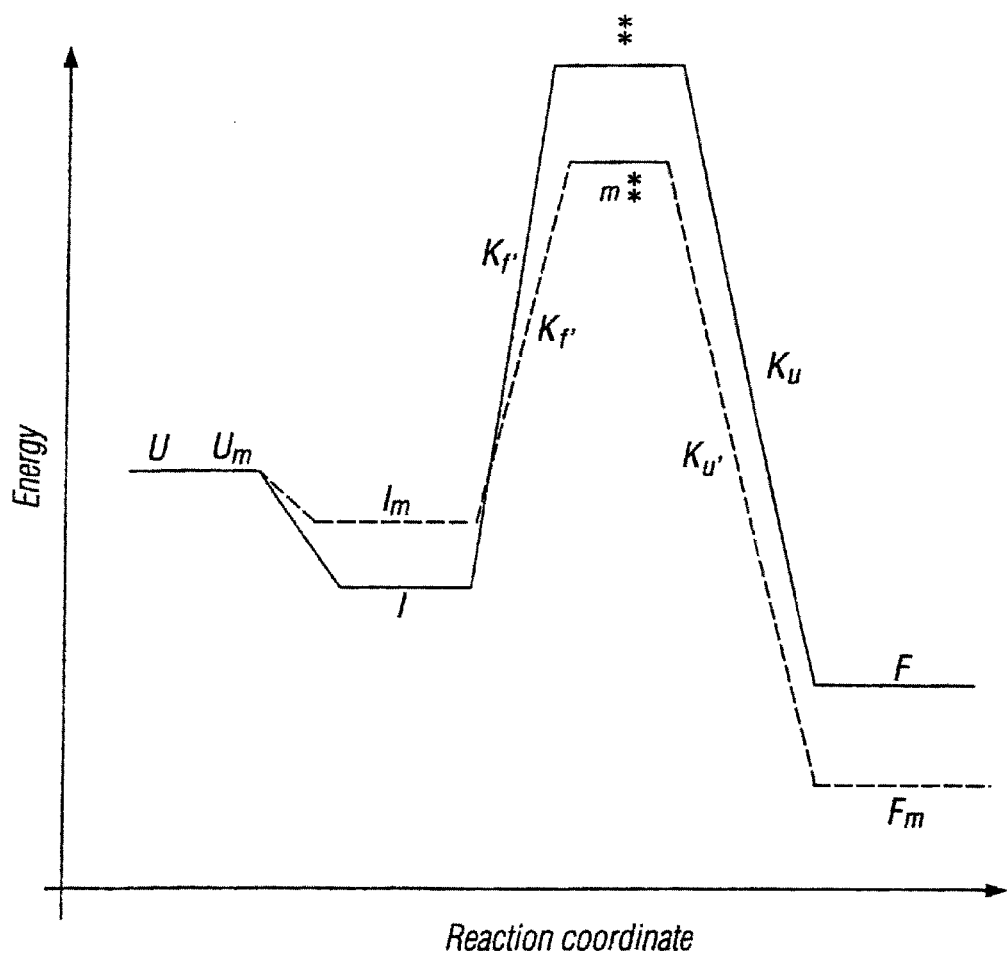
FIG. 3: Acceleration of the folding reaction through the optimization of local interactions. U represents the unfolded conformational ensemble, I and F, $I_m$, and $F_m$, represent, respectively, the intermediate and the folded state in the wild type protein and in the mutant. $K_u$ and $K_f$ are the unfolding and folding rate constants, and ‡ symbolizes the transition state.
Figure 4:
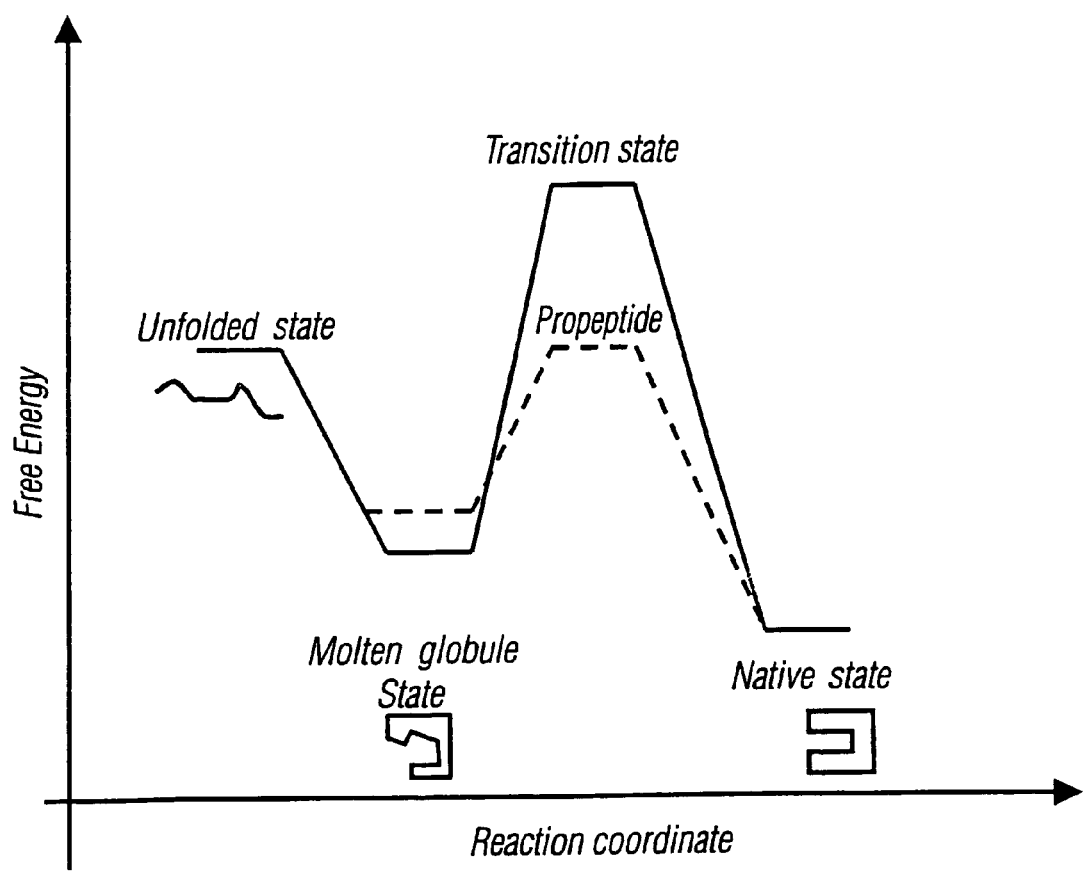
FIG. 4: Possible pathway by which intramolecular chaperones mediate protein folding. When the protein folds in the absence of its pro-sequence, it acquires a molten globule state conformation, which possesses native-like secondary structure but lacks the tertiary interactions required for biological activity. The molten globule is stable and it is unable to surmount the energy barrier that separates it from the folded state. Addition of the propeptide lowers the energy barrier between the molten globule state and the transition state, allowing fold to proceed to the native state.
Figure 5:
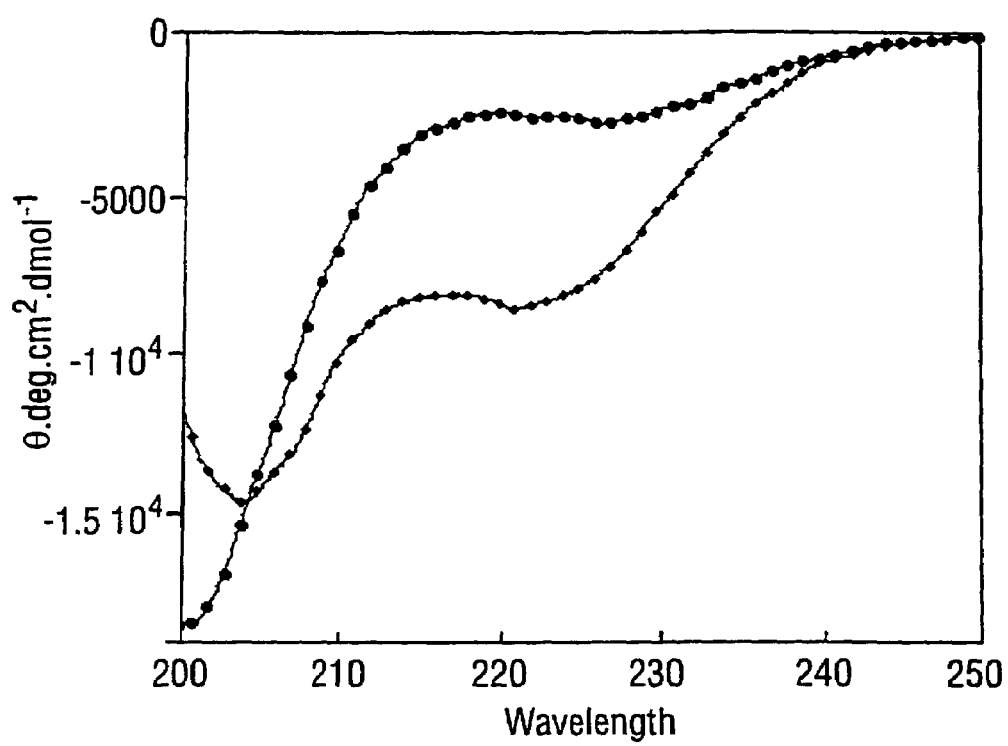
FIG. 5: Far-UV CD spectra of the wild-type, (●) and mutant (♦) peptides of helix C of IL-4 in 25 mM Na$_2$HPO$_4$, pH 6.5, at 5° C. The values predicted by AGADIR1s-2 for the helical content of the peptides and the experimentally determined values are inserted
Figure 6:
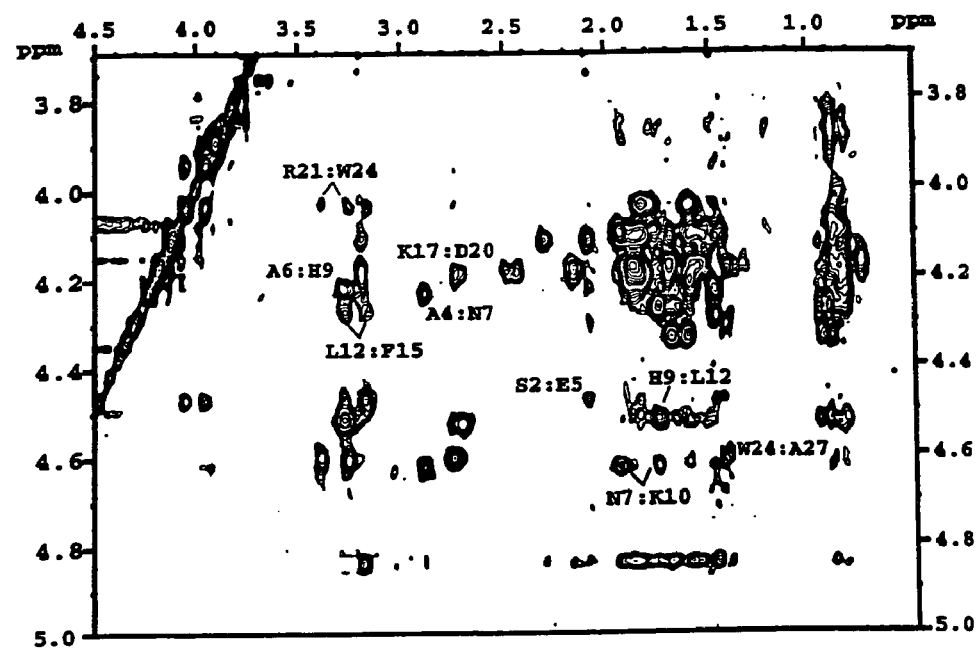
FIG. 6: Comparison of the 2D NOESY spectra of the wild type (IL4Ch_wt) and mutant peptide (IL4BCh). The spectra were acquired with a mixing time of 140 ms. The thickness of bar beneath the sequence of the peptides represents the organization of the helix in IL4BCh based on the NOE data.
Figure 6:
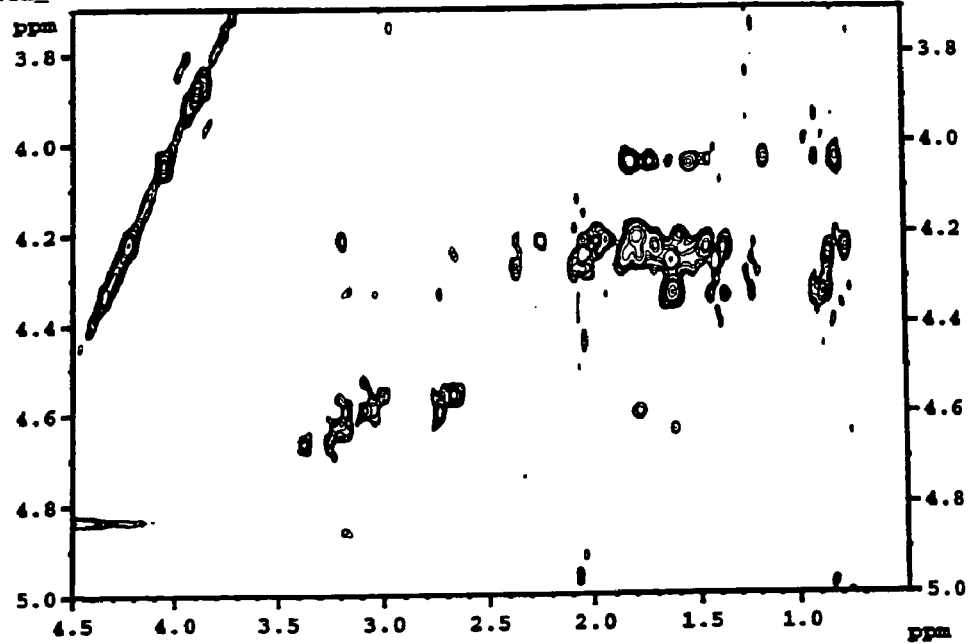
Figure 7:
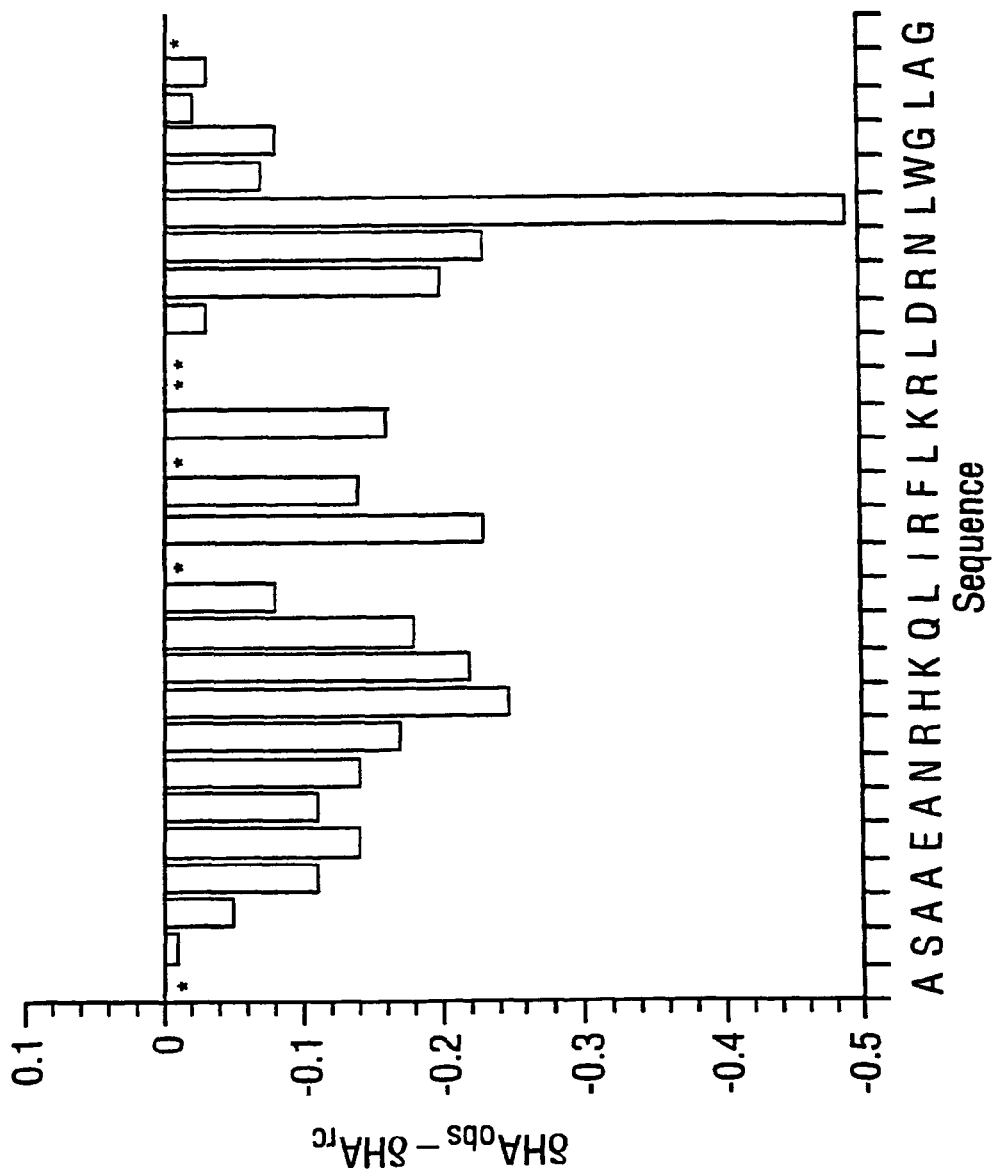
FIG. 7: Difference between the chemical shift values of the Hα protons of the mutant peptide and the random coil values (Merutka et al., 1995). Negative values indicate the formation of helical structure. Residues whose Hα could not be unambiguously assigned, are marked by an asterisk (*).

Rationally Designed Mutagenesis to Prevent the Aggregation of hIL-4

Interleukin-4 forms inclusion bodies upon overexpression in *E. coli* and the in vitro refolding of the protein is very inefficient, yielding only a very small amount of active protein. Aggregation both in vitro and in vivo is thought to result mainly from the accumulation of folding intermediates which have a high tendency to associate (Filimonov et al., 1993) and establish non-native interactions that direct the protein to inactive conformations (Booth et al., 1997).

We have used two different strategies in order to selectively destabilize any putative intermediate in the folding pathway of IL-4.

1.1 METHOD

Cloning

The IL-4 gene has been obtained by PCR from a previously described plasmid, R$^{15}$prC109/IL4 (Kruse et al., 1991), NcoI and BamHI were introduced at the 5' and 3' ends, respectively, using the following oligonucleotides: Oligo5': CTG GAG ACT G<u>CCATGG</u>AT CAC AAG TGC GAT; Oligo3': A CGC <u>GGATCC</u> TTA TCA GCT CGA ACA. The gene coding for the wild type IL-4 and for the mutant proteins was inserted into PBAT4 (Peränen et al., 1996) between the NcoI and BamHI cloning sites. Due to the introduction of a NcoI site at the 5' end, wild type IL-4 and the IL-4 mutant proteins are expressed with an additional amino acid (Asp) at the N-terminus.

Site-Directed Mutagenesis

The mutants IL-4W91S and IL-4BChelix were obtained by PCR (Ho el al., 1989) using oligo 5' and oligo 3' as flanking sequences, and the following mutagenic primers (5' to 3'): IL-4L23Sa: CAG AGC AGA AGA CTA GTT GCA CCG AGT TGA CCG; IL-4L23Sb: CGG TCA ACT CGG TGC AAC TAG TCT TCT GCT CTG, IL4W91Sa: AGG AAC CTC AGT GGC CTG GCG GGC TTG; IL-4-W91Sb: CAA GCC CGC CAG GCC ACT GAG GTT CCT, IL-4BChelixa: CTG GGT GCG AGT GCA GCA GAA GCA AAC AGG CAC AAG C, IL-4BChelixb: G CTT GTG CCT GTT TGC TTC TGC TGC ACT CGC ACC CAG. The double mutant IL-4L23S W91S was generated using IL-4L23S as a template for the PCR reaction and the IL-4W91S primers listed above.

Peptide Synthesis

Peptides were synthesised on polyoxyethylene-polystyrene graft resin in a continuous flow instrument. Peptide chain assembly was performed using Fmoc chemistry (Carpino et al., 1972) and in situ activation of amino acid building blocks by PyBOP (Coste et al., 1990). The peptide was purified by reversed phase HPLC and characterized by laser desorption mass spectrometry (MALDI).

1.2 Replacement of Exposed Hydrophobic Residues in the Folded State By Polar Ones Folding intermediates are often characterized by the presence of a significant amount of secondary structure and ill-defined tertiary structure, being stabilized by hydrophobic interactions. Therefore, it is quite plausible that hydrophobic residues that are exposed in the folded state as a result of the tertiary fold, will be buried in a folding intermediate. Mutation of these residues to a polar amino acid should destabilize the intermediate with respect to the folded state, through the so-called inverse hydrophobic effect (Pakula & Sauer, 1990).

Two non-conserved solvent exposed amino acid residues were identified in IL-4: Trp 91 and Leu L23. In most of the other members of the IL-4 family a serine is found at the corresponding positions, and therefore this amino acid was chosen to replace W91 and L23 in the human protein. The two point mutants thus obtained are designated IL-4W91S and IL-4L23S, and a mutant carrying both mutations, IL-4L23SW91S.

1.3 Stabilization of Secondary Structure Elements

Secondary structure elements are stabilized by a set of local interactions between neighbouring residues.

1.3.1 Stabilization of α-Helices Using AGADIR

AGADIR is based on empirical data derived from conformational studies of monomeric peptides in solution. The algorithm uses this information to calculate the free energy of a given helical segment ($\Delta G_{helix}$), based on the helix-coil transition theory. This free energy reflects the contribution of different interactions within the helix, and corresponds to the difference in free energy between the random coil and helical states. In the newest version of the algorithm (AGADIR1s-2, Lacroix el al., 1998), the free energy of a helical segment is described according to the following:

$$\Delta G_{helix} = \Delta G_{int} + \Delta GH_{bond} + \Delta G_{SD} + \Delta G_{nonH} + \Delta G_{dipole} + \Delta G_{elect}$$

where $\Delta G_{int}$ is the intrinsic tendency of a given amino acid to be in the helical conformation (Muñoz et al., 1994e) and represents the loss of conformational entropy which occurs upon fixing an amino acid in helical dihedral angels. $\Delta GH_{bond}$ is the enthalpic contribution of the i,i+4 main-chain-main-chain hydrogen bonds; $\Delta G_{SD}$ represents the contributions of the side-chain-side-chain non-charged interactions at positions i,i+3 and i,i+4 in the helical segment. For amino acid residues with ionizable side chains, the pH dependence of these type of interactions is taken into account. $\Delta G_{dipole}$ reflects the interaction of charged groups, within or outside the helical segment, with the helix macrodipole. Another type of interaction that is independent of the presence of charged groups has to do with the increase in stability of α-helices observed upon increasing the ionic strength (Scholtz et al., 1991). Because α-helices have a much larger dipole moment than the random coil, increasing the ionic strength preferably stabilizes the α-helix, shifting the equilibrium towards this conformation. This effect is also taken into account by AGADIR1s-2 by considering the difference in the folding free energy of a particular α-helix in a solution with a given ionic strength and in pure water. $\Delta G_{elect}$ includes all electrostatic interactions between two charged residues inside and outside (Ncap and residue preceding the Ncap, and Ccap and residue following the Ccap) the helical segment with the helix macrodipole and residues within the helix. The electrostatic interactions are calculated taking into account the effect of charge screening upon increasing the ionic strength, and the average distance between two interacting charged groups has been derived from a statistical analysis of the database. The charges of the individual amino acids in the random coil and helical conformation are determined by calculating their pKa and taking into account the pH dependence. AGADIR1s-2 also considers the effect of N- and C-terminal blocking groups. The residues following the acetyl group at the N-terminus or preceding the amide group at the C-terminus are allowed to adopt helical angles with the acetyl and amide groups playing the role of the capping residue.

1.3.2 Stabilization of Helix C of IL-4

α-helix C of IL-4 was selected as the target for several reasons. This helix is not very conserved among the members of the IL-4 family; it is known that the first residues at the N-terminus are not involved in binding to the receptor (Wang el al., 1997); and Nuclear Magnetic Resonance $^{15}N$ relaxation and hydrogen exchange studies on IL-4 have shown that this region of helix C is very flexible (Redfield et al., 1992; Redfield et al., 1994a; Redfield el al., 1994b). In fact, AGADIR1s-2 predicts a low average helical content (4%) for this helix.

Using AGADIR1s-2 we have designed three different types of mutations that increase the average helical content up to 20% and increase the stability of the α-helix by about 1.8 Kcal/mol. Essentially, we have replaced the N-capping box motif present in the wild type protein (T—X—X—Q) by a better counterpart (S—X—X—E). Better helix formers (Chakrabartty et al., 1995; Muñoz et al., 1994e) have been introduced into the sequence of the helix: Q71 and F73, were mutated into alanine, and H74 was substituted by an asparagine. The reason why asparagine was preferred over alanine to replace H74 is that, introduction of yet another alanine at this position would result in a hydrophobic cluster at the N-terminus comprising five alanine residues, that could reduce the solubility of the protein and produce aggregation. Finally, we have introduced two favorable electrostatic pairs (E—X—X—R and E—X—X—X—H).

No mutations were designed at the C-terminus of the helix because it contains part of the functional IL-4 epitope (Wang et al., 1997). Moreover, a Schellman motif (Schellman et al., 1980) between a leucine residue at position 93 and the arginine at position 88 is present in the wild type sequence. This motif should involve the formation of two main-chain/main-chain hydrogen bonds between these two residues, and is expected to contribute about 1 Kcal/mol to the helix stability (Viguera et al., 1995). The mutant bearing the stabilized helix C will be herein designated IL-4BChelix.

Circular Dichroism shows a clear increase in the helical content of the mutant peptide. The values predicted by AGADIR1s-2 for the helical content of the wild type and mutant peptide are in excellent agreement with the ones determined experimentally from the ellipticity value at 222 nm (see FIG. 5).

Nuclear magnetic resonance studies of the wild type (IL4Ch_wt) and mutant peptides (IL4BCh) have been performed (see FIG. 6) For IL4Ch_wt none of the NOE indicative of the formation of a helical structure could be found, whereas in the case of IL4BCh, we have been able to assign unambiguously long range dαβ(i,i+3) NOEs (Wütrich et al., 1996) throughout the entire sequence of the peptide. The NOE data reveal the formation of a capping box motif at the N-terminus of IL4BCh, between S2 and E5, and a well-defined helical region spanning residues S2-F15. The region between residues F15–D20 is less well defined, and at the C-terminus two long range NOEs connecting R21 to W24 and W24 to A27 are observed.

The conformational shifts of the Hα protons (FIG. 7) provide further evidence for the formation of the α-helix in the mutant peptide. Residues I13, L16, R18 and L19 could not be unambiguously assigned due to overlap with other resonances in the spectra. L23 shows a large deviation of the alpha proton chemical shift to higher field due to the proximity of the tryptophan residue.

EXAMPLE 2

In Vivo Folding of the IL-4 Variants

The designed mutants and the wild type protein were overexpressed in three different *E. coli* strains, in a number of different conditions.

Only DE3 strains were used to allow expression with T7-based expression plasmids. These strains contain a chromosomal copy of the T7 RNA polymerase gene under lacUV5 control. Addition of IPTG to the growth medium, induces transcription of T7 RNA polymerase which can then mediate the transcription of the target gene under the control of the T7 promoter in the expression plasmid (Furlong et al., 1992).

Figure 8:
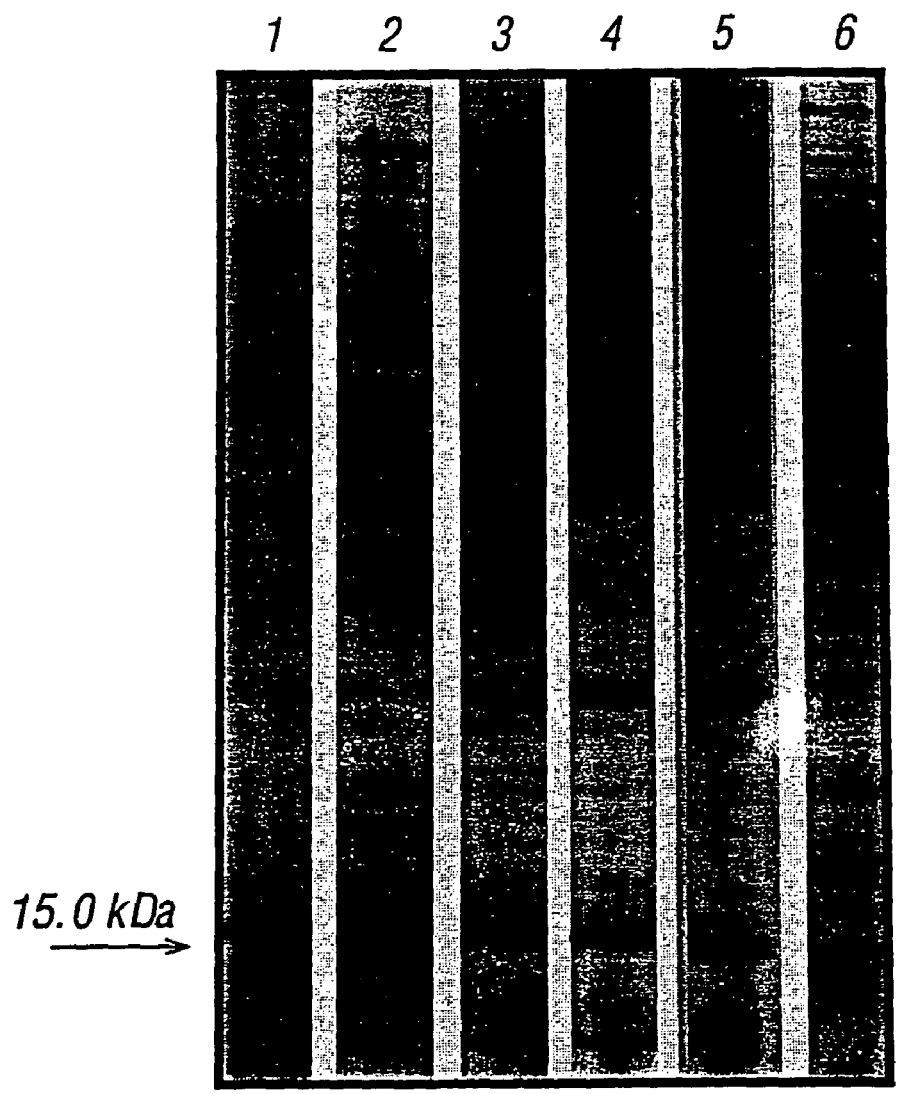
FIG. 8: Cellular fractions derived from *E. coli* AD494 expressing IL-4 WT and the mutant proteins. Lane 1: insoluble fraction of IL-4L23SW91S, lane 2: soluble fraction of IL-4L23SW91S, lane 3: soluble fraction of IL-4L23S, lane 4: soluble fraction of IL-4W91S, lane 5: soluble fraction of IL-4BChelix, lane 6: Soluble fraction of the wild type protein. Only a very small fraction of the wild type protein (less than 10%) is found in the cell supernatant, in contrast with 50%–60% of the mutant proteins, as determined by densitometric analysis of the SDS gel.

Both the wild type protein and the mutants were expressed to high levels in the different strains, making up to 60% of the total cellular protein. IL-4WT invariably formed inclusion bodies in the three strains, under all the conditions tested. However, when the mutants (IL-4L23S, IL-4W91S, IL-4L23SW91S, and IL-4BChelix) where overexpressed in AD494, a thioredoxin reductase deficient strain (trxB'), around 50% of the produced protein was found in the supernatant (FIG. 8).

Because AD494 lacks one of the main reducing pathways, disulfide bonds should in principle be allowed to form in the E. coli cytoplasm (Derman et al., 1993). Indeed, this strain has already been used to improve the solubility of several proteins that form inclusion bodies when produced in the more conventional expression strains like BL21. Expression of the IL-4 mutants in BL21 also resulted in protein aggregation. Furthermore, the solubility of the proteins was not increased upon co-expression with the GroEL/ES chaperonin system, or thioredoxin, although the expression level was significantly reduced.

Expression of the proteins in any of the strains at lower temperatures (15° C.–30° C.) was found to have no effect on the amount of soluble product, nor was the concentration of inducer used to initiate expression.

The results described above are summarized in Table 2 below.

Table 2 Summary of the strategies used to reduce the formation of IL-4 inclusion bodies 1B). The optical density of the cells at at 600 nm is denoted by IOD and expression with or without the pro-sequence is represented, repectively, by +pro/−pro.

EXAMPLE 3

Characterization of the Soluble IL-4 Mutants 3.1 Methods

Solubility Tests

*Escherichia coli* AD494 (DE3), BL21 (DE3) and W3110 (DE3) were transformed with the plasmids coding for the IL-4WT and the mutant proteins. In each case, 1 L flasks with LB medium were inoculated with a single colony and incubated on a shaker at temperatures ranging from 15–37° C., in the presence of 100 mg/l of ampicilin. Protein expression was induced at $OD_{600}$ 0.4–1.0, at different temperatures, using IPTG concentrations ranging from 0.1 to 1 mM. In the case of BL21 (DE3) and W3110 (DE3) the culture was incubated for 3 h after induction, and the cells harvested by centrifugation. In the case of AD494 (DE3) protein expression was induced overnight. In all cases, the harvested cells were resuspended in 25 mM Tris-HCl pH 8.0. Cell disruption was initiated by incubating the cells with 1 mM $MgCl_2$, 20 ug/ml lysozyme and 10 ug/ml DNAse and then completed using a French Pressure Cell. The soluble fraction was separated from the cell debris by ultra-centrifugation at 40000 rpm, for 1 hour. Samples from the soluble and insoluble fraction were collected and analysed by SDS-PAGE on a 12% polyacrylamide gel. Quantification of the soluble and insoluble product was done by densitometric analysis of the gel.

Co-Expression with GroEL/S and Thioredoxin

In order to overexpress the proteins with the GroEL/ES chaperonins and thioredoxin, competent cells of BL21 carrying PT-groE or PT-Trx were transformed with the plasmids coding for each of the muteins and for IL-4 wild type. Bacteria were grown from a single colony in 1 shaking flasks containg LB, at temperatures ranging from 30–37° C., in the presence of 100 mg/l of ampicilin and 50 mg/l of chloramphenicol. Expression of the IL-4 variants and the chaperones was simultaneously induced upon addition of IPTG to the

| | Strain (DE3) & Vectors | | | | | |
|---|---|---|---|---|---|---|
| | BL21 | | | W3110 | AD494 | |
| | PBAT4 | | | & | & | Expression |
| Protein | −pro | +pro | PT-trx | PT-groE/S | PBAT4 | PBAT4 | Conditions |
| IL4WT | IB | IB ↓Exp | IB ↓Exp. | IB ↓Exp. | IB | IB | 15–37° C. 0.10–1 mM IPTG IOD = 0.4–0.9 |
| IL4L23S | IB | IB ↓Exp | IB ↓Exp. | IB ↓Exp. | IB | 50% Soluble | 37° C. 0.16 mM IPTG IOD = 0.7–1.0 |
| IL4W91S | IB | IB ↓Exp | IB ↓Exp. | IB ↓Exp. | IB | 50% Soluble | 37° C. 0.16 mM IPTG IOD = 0.7–1.0 |
| IL4L23SW91S | IB | IB ↓Exp | IB ↓Exp. | IB ↓Exp. | IB | 50% Soluble | 37° C. 0.16 mM IPTG IOD = 0.7–1.0 |
| IL4BChelix | IB | IB ↓Exp | IB ↓Exp. | IB ↓Exp. | IB | 60% Soluble | 37° C. 0.16 mM IPTG IOD = 0.7–1.0 | growth medium to a final concentration of 0.16 mM, once an $OD600_{mm}$ of 0.7 was reached.

Expression of Soluble Protein in AD494

Escherichia coli AD494 (DE3), was transformed with the plasmids coding for the IL-4WT and the mutant proteins. 1 L flasks with LB medium were inoculated with a single colony and incubated on a shaker at 37° C. After an $OD_{600}$ of 0.7–0.8 was reached. IPTG was added resulting in a final concentration of 0.16 mM. The culture was incubated overnight and the cells were harvested by centrifugation.

Purification of Soluble Protein

The harvested cells were resuspended in 25 mM $NaH_2PO_4$, pH 6.5 and incubated on ice for 1 hour, with 1 mM $MgCl_2$, 20 ug/ml lysozyme and 10 ug/ml DNAse and then lysed further using a French Pressure Cell. The soluble fraction was separated from the cell debris by ultra-centrifugation at 40000 rpm, for 1 hour. Samples from the soluble and insoluble fraction were analysed by SDS-PAGE on a 12% polyacrylamide gel. Quantification of the soluble and insoluble product was done by densitometric analysis of the gel.

Protein purification was carried out on a FPLC system from Pharmacia. The cell supenatant was first run through a Sepharose S column (Pharmacia) pre-equilibrated with 25 mM $NaH_2PO_4$ pH 6.5. The elution of the protein was carried out by running a linear salt gradient from 0–0.5 M NaCl. The four IL-4 variants eluted at 120 mM NaCl. The collected fractions were then submitted to size exclusion chromatography and the proteins purified up to 90% homogeneity. The yield of the purification process was such that 1 mg of IL-4L23S, IL-4W91S, IL-4L23SW91S were obtained per liter of cell culture, and around 2 mg of IL-4 BChelix.

Protein Expression as Inclusion Bodies in AD494

Was carried out as described above for the production of soluble protein, with the exception that protein expression was induced at $OD6_{00}$ of 0.5.

Fermentation on the 10 and 100 L Scale

In order to produce larger amounts of protein, fermentations in a 10 l bioreactor were performed. For these fermentations the plasmids were transformed into E. coli W3110 (DE3). The cells were grown by batch fermentation at 37° C. in a complex medium (30 g/L soya peptone, 20 g/L yeast extract, 20 g/L glycerol, 5 g/L $KH_2PO_4$, 1 g/L $MgSO_4$, 100 mg/l ampicillin) to an $OD_{600}$ of 3.0. At this stage expression of the recombinant protein was induced by the addition of 0.4 mM IPTG. After an induction phase of 4 hours cells were harvested by centrifugation.

Protein Purification from Inclusion Bodies

The harvested cells were resuspended in 25 mM Tris-HCl pH 8.0. Cell disruption was performed enzymatically by the addition of lysozyme (1 mg per g cell dry weight) and incubation at room temperature for 30 min. Released inclusion bodies were harvested by centrifugation at 8000 g (30 min). The pellets were washed four times by resuspension in 0.1 M Tris-HCl/1 mM EDTA/0.1% zwittergent 3–14 buffer pH 8 and centrifugation (8000 g, 15 min). Washed inclusion bodies were solubilized in 8 M GdnHCl/0.1 M Tris-HCl, pH 9. SH-groups were modified to $S-SO_3$ by the addition of excess sulfite and tetrathionate as described by (Kella et al., 1988; Kella el al., 1985).

Refolding was carried out at a protein concentration of 200–300 mg/L, by cross-flow ultrafiltration against five volumes of 50 mM $Na_2HPO_4$ pH 7, 1 mM EDTA, 0.4 mM L-cystein, 0.6 mM arginine, during 5 hours (one volume exchange/hour). In-process analysis was performed by RP-HPLC on a Vydac C4 resin, applying a linear gradient of Trifluoracetic acid-Acetonitrile. Refolding yields were obtained by comparing the percent ratio of the peak area of correctly folded isoform to the total peak area (total protein).

Circular Dichroism

The far UV CD spectra were recorded, on a Jasco-710 instrument, in a cuvette with a 2 mm path. Measurements were made every 0.1 nm, with a response time of 2 s and a bandwidth of 1 nm, at a scan speed of 50 nm/min. The spectra shown in the text represent an average over 20 scans. The protein concentration, calculated from the absorbance at 280 nm (Pace et al., 1995), was 10 µM. The experiments were carried out in 25mM $Na_2HPO_4$, pH 6.5 at 5° C.

Thermal Denaturation

Thermal denaturation was measured, by monitoring the change in signal at 222 nm over a temperature range of 6–90° C., in a cuvette with a 2 mm path. Measurements were made in 0.5 degrees increments, with a response time of 2 s and a bandwidth of 1 nm, at a temperature slope of 50° C./h. The protein concentration calculated from the absorbance at 280 nm was 10 µM (Pace et al., 1995) and the measurements were carried out in 25 $NaH_2PO_4$ mM pH 6.5. The curves were fitted with a two state model using the midpoint temperature ($T_m$), the enthalpy change at the midpoint temperature ($\Delta H_m$) and the excess heat capacity change ($\Delta C_p$) as fitting parameters, according to the equation below:

$$F_{unf}=F_N+F_U*exp\{(\Delta H_{(T_m)}(1/T_m-1/T)+\Delta C_p(\ln(T/T_m)-(T-T_m)/T))/R\}/(1+exp\{(\Delta H_{(T_m)}(1/T_m-1/T)+\Delta C_p(\ln(T/T_m)-(T-T_m)/T))/R\})$$ Eq. 1 where $F_{unf}$ represents the fraction of unfolded protein as a function of temperature (T), and $F_N$ and $F_U$ represent, respectively, the fraction of fully native and fully unfolded protein obtained by the linear fitting of the baselines preceding and following the transition region.

Chemical Stability

Chemical denaturation and renaturation experiments were carried out at 25° C., in 50 mM $Na_2HPO_4$ pH 6.5. The protein concentration used was 7 µM for IL-4 wild type and for IL-4W91S, and 5 µM for IL-4BChelix. The Jasco automatic titration system was used to mix the denaturant and the protein. The GdnHCl concentration was calculated by measuring the refractive index of the solution, as described by Pace et al. (1990). The unfolding and refolding of the protein were monitored following the change in the CD signal at 222 nm. The ellipticity readings were normalized to fraction unfolded using the standard equation:

$$F_{unf}=(\theta-\theta_N)/(\theta_D-\theta_N)$$ Eq. 2 where $\theta$ is the ellipticity value at a certain concentration of denaturant, and $\theta_N$ and $\theta_D$ stand for the ellipticities of the fully native and fully unfolded species at each denaturant concentration, and were calculated from the linear regression of the pre and post-unfolding baselines. Assuming a two state model, the equilibrium constant for denaturation, at each denaturant concentration, can be calculated using the equation below:

$$K_D=(F_N-F)/(F-F_U) \quad \text{Eq. 3}$$

where $F_N$ and $F_U$ represent, respectively, the fraction of fully native and fully unfolded protein obtained by the linear fitting of the baselines preceding and following the transition region. It has been found experimentally that the free energy of unfolding in the presence of GdnHCl is linearly related to the concentration of denaturant (Pace, 1986):

$$\Delta G_D = \Delta G^{H_2O} - m[GdnHcl] \quad \text{Eq. 4}$$

The value of m and $\Delta G_D^{H_2O}$, the apparent free energy of unfolding in the absence of denaturant, can be calculated from $$\Delta G_D = -RT \ln K_D \quad \text{Eq. 5}$$

The proportionality constant m reflects the cooperativity of the transition and is believed to be related to the difference in hydrophobic surface exposed to the solvent between the native and the denatured states. When all these dependencies are taken into account, the change in ellipticity as a function of the concentration of denaturant, can be fitted to the following equation:

$$F_{unf} = \{(F_N + a[GdnHCl]) + (F_U + b[GdnHcl])\exp\{(m[GdnHcl] - \Delta G_D^{H_2O}/RT\}/\{1 + \exp((m[GdnHCl] - \Delta G_D^{H_2O})/RT)\} \quad \text{Eq. 6}$$

in which the dependence of the intrinsic ellipticity upon denaturant concentration, in both the native and the denatured states, is taken into account by the terms of a [GdnHCl] and b [GdnHCl], respectively (linear approximation Santoro & Bolen, 1988).

NMR Spectroscopy

NMR samples of IL-4 and the mutant proteins were prepared by dissolving the lyophilized protein in 45 mM deuterated sodium acetate (NaOAcd$_4$) pH 5.3 10% D$_2$O, 0.1 mM TSP, 0.2% NaN$_3$ to give a protein concentration of 500 μM. The spectra were recorded at 303 K using standard pulse sequences and phase cycling.

Receptor Binding Assay

The binding affinities were measured by surface plasmon resonance using a BlAcore 2000 (Pharmacia Biosensor). A recombinant extracellular domain of the receptor α-chain ([C182A,Q206C] IL4-BP) was immobilized at a biosensor CM5 to a density of 1500 to 2000 pg/mm$^2$, as described by Shen et al. (1996). Binding was analyzed at 25° C. by perfusion with HBS buffer (10 mM Hepes, psH 7.4/150 mM NaCl/3.4 mM EDTA/0.005% surfactant P20) plus 0.5 M NaCl at a flow rate of 50 μl/min.

3.2 Results

The product present in the soluble cellular fraction was purified by action exchange chromatography, taking advantage of the high PI of IL-4 (9.2), followed by a gel filtration step. Around 1 mg of IL-4L23S, IL-4W91S and the double mutant, IL-4L23SW91S was obtained from 1 L of cell culture.

The yield was slightly higher for the C helix mutant, IL-4BChelix, with 1.6 mg purified per liter of culture, IL-4L23S, and to a less extent IL-4L23SW91S, were extensively degraded during the purification and precipitated when concentrated to 1 mg/ml. However, IL-4W91S and IL-4BChelix behaved better and did not precipitate when concentrated down to 1 mg/ml.

In order to investigate whether these two proteins were folded, far UV CD spectra were recorded on the purified samples and compared to the spectrum of the wild type protein (data not shown). The CD spectra of both IL-4W91S and IL-4BChelix display the shape expected for a protein with high content of α-helix, but differ from the spectrum of IL-4WT, particularly in the wavelength range between 210–225 nm. Both mutants displayed a well defined minimum at 208 nm like the wild type protein, but in the case of IL-4BChelix, the signal at 222 nm was less negative than expected. This effect is unlikely to arise from a stronger contribution from the random coil signal because this protein exhibits a cooperative temperature unfolding transition with a Tm of 54° C. The observed decrease in ellipticity at 222 nm probably reflects the contribution of some parts of the protein that might be less structured.

A cooperative temperature induced transition was also observed for IL-4W91S (data not shown), suggesting the presence of tertiary interactions in both mutants. In this case, the ellipticity values between 208–220 nm are more negative than in the wild type protein, and the minimum at 222 nm is shifted to 218 nm. These differences are difficult to interpret because of the removal of the tryptophan residue. Aromatic residues contribute to the far UV CD signal but this contribution depends on the environment in which the residue is located and is difficult to predict.

However, the temperature-induced transition was not completely reversible for both mutants, with only 50% of the signal recovered after cooling the samples back from 90 to 5° C. and part of the samples precipitated in the cuvette during the experiment. Besides, the samples were unstable and precipitated upon freeze-thawing. Mass Spectrometry and SDS-PAGE analysis identified several low molecular weight species indicative of degradation in both samples. Neither IL-4W91S or IL-4BChelix were able to bind IL-4Rα, as determined in a plasmon resonance experiment.

3.2.1 In Vitro Characterization of IL-4W91S and IL-4BChelix

The fact that the IL-4 mutants produced soluble in *E. coli* were not able to bind the IL-4 receptor, suggests that these proteins are not properly folded. However, we thought it would be interesting to look at the in vitro refolding behaviour of these mutants. Our idea was that although the protein present in the supernatant was not active, the fraction in the inclusion bodies could still refold in vitro more efficiently than the wild type protein.

IL-4WT and the two mutants, IL-4W91S and IL-4BChelix, were overexpressed in AD494. This time the expression conditions were optimized for maximization of protein production instead of solubility. Higher expression levels were obtained when the cells were induced at an optical density of 0.4–0.5 with 0.16 mM IPTG. Protein purification from the inclusion bodies and the in vitro refolding was performed according to procedures previously described (Kato et al., 1985; Weigel et al., 1989).

3.2.2 Refolding Yield and Activity Assays

We have measured the binding constants of the IL-4W91S and IL-4BChelix renatured from the insoluble cellular fraction to the IL-4Rα receptor (see Table 3).

TABLE 3

In vitro Refolding Yield and $k_d$ of IL-4 wild type and the designed Mutants

| Protein | Refolding Yield (%) | $K_d$(nM) |
| --- | --- | --- |
| IL-4 wild-type | 13 | 1.52 |
| IL-4 W91S | 15 | 2.95 |
| IL-4 BChelix | 23 | 1.64 |

Figure 9A:
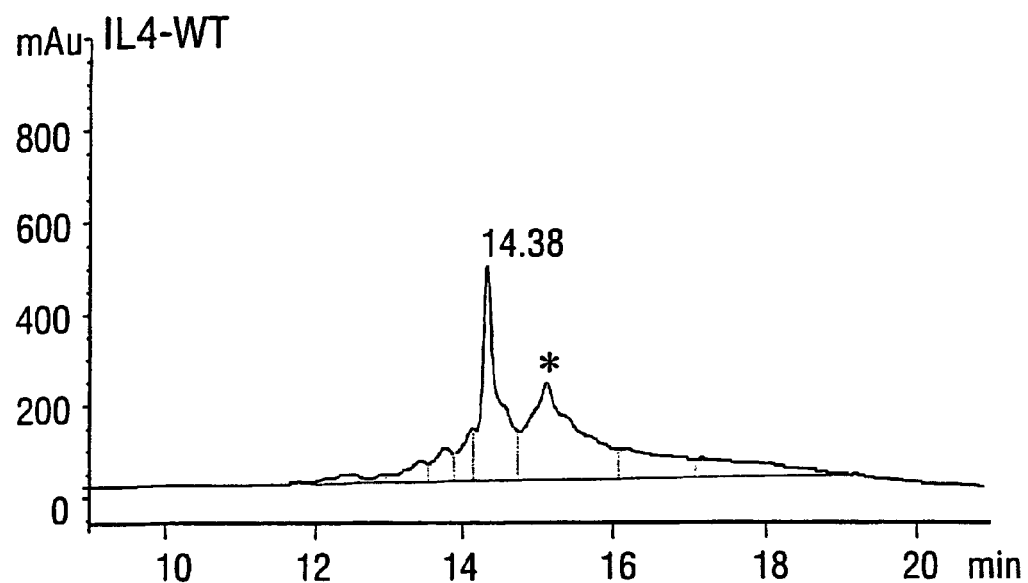
FIG. 9: HPLC of wild type IL-4 (panel A) and mutant IL-4Bchelix (panel B) proteins.
Figure 9B:
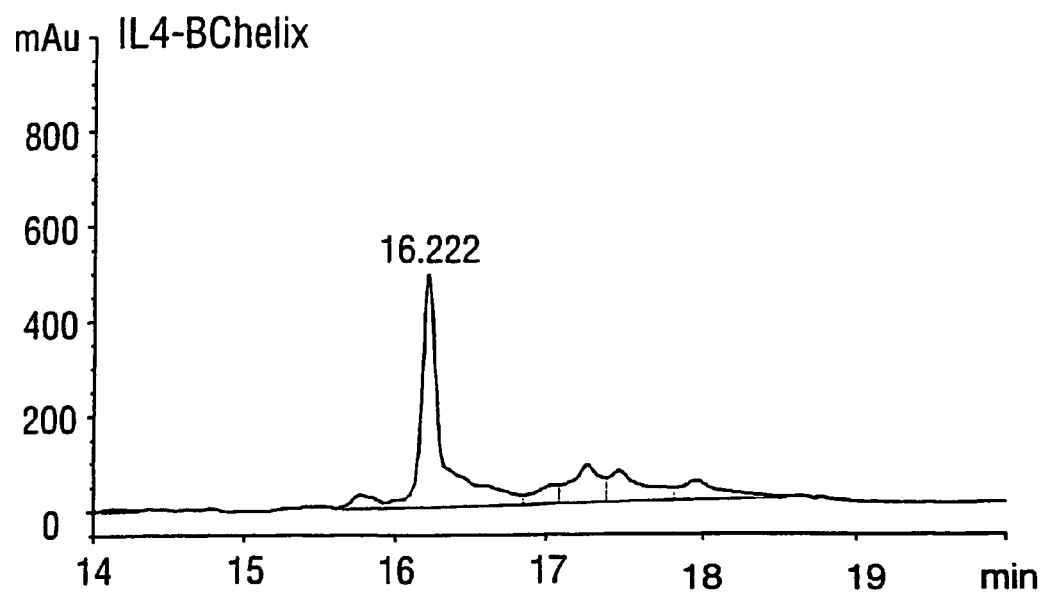

The refolding yields of IL-4WT and the mutant proteins are shown in Table 4. These values represent the amount of correctly refolded protein and are an average over the data obtained in four independent experiments. In two of these experiments, the proteins were overexpressed in 1 L shaking flasks, as described under methods. In another two experiments, IL-4WT and the two mutant proteins were isolated from cells obtained after low cell density fermentation on the 10 L and 100 L scale (see methods). In the four experiments, IL-4BChelix refolds with a yield approximately two-fold that of IL-4WT, while the $K_d$ for IL4Rα remains identical to that of the wild type protein. Preliminary data on the oxidative refolding of IL-4 suggest that the observed increase in the refolding yield of IL-4BChelix results from the destabilization of a non-native isoform which accumulates during the refolding of the wild type protein (see FIG. 9). On the other hand, replacement of W91 by serine does not improve the refolding of the protein. Moreover, this mutation leads to a two-fold decrease in binding affinity to IL4Rα, which is in a good agreement with previous studies, suggesting a small role for W91 in receptor binding (Wang el al., 1997).

3.2.3 Thermodynamic and Structural Characterization of the Proteins

Figure 10:
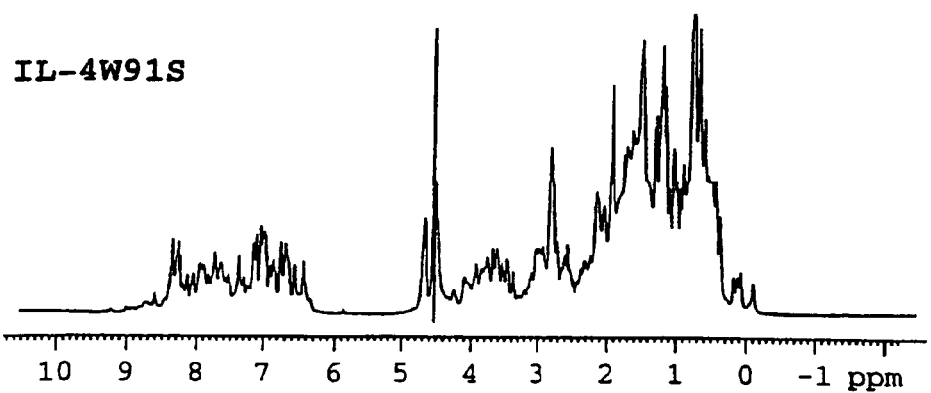
FIG. 10: Mono-dimensional NMR Spectra of IL-4 WT, IL-4W91S and IL-4BChelix. The good dispersion of the NMR signals shows that the proteins are folded.
Figure 10:
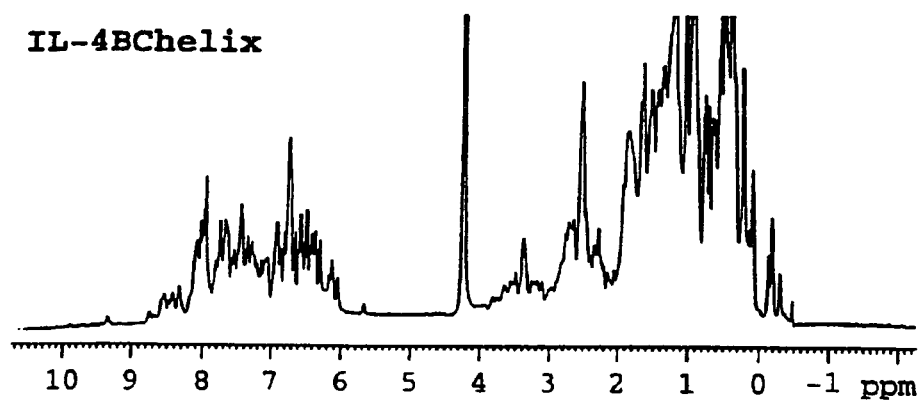
Figure 10:
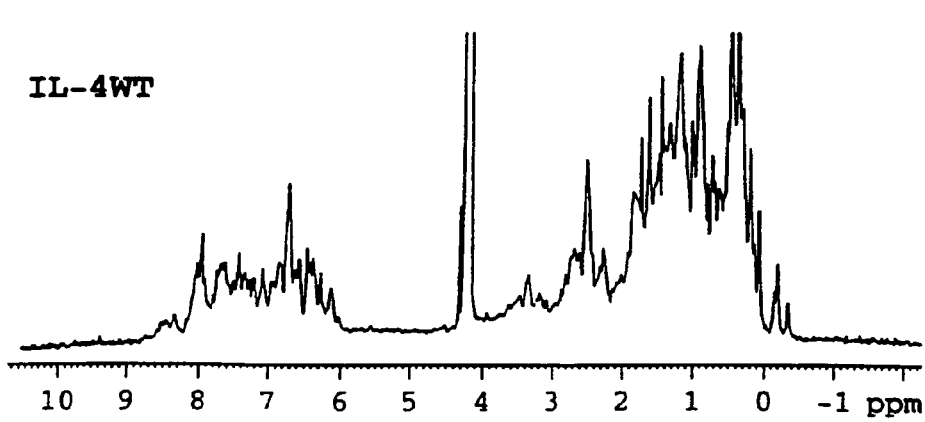

The purified samples of IL-4W91S and IL-4BChelix display NMR spectra that are similar to that of the wild type (FIG. 10).

Figure 11A:
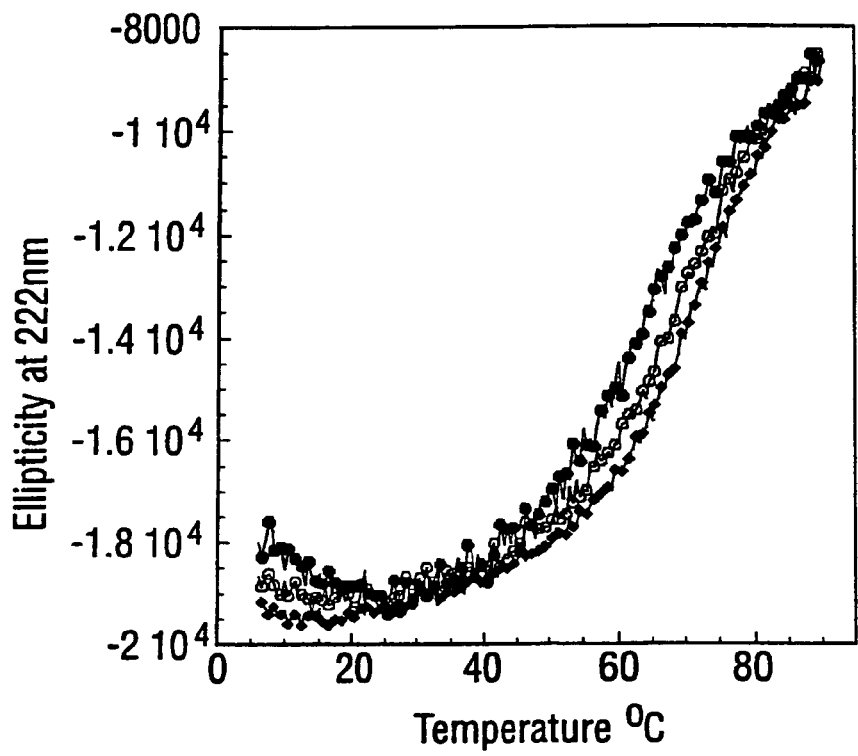
FIG. 11: a Temperature denaturation profile of IL-4 WT (●) and the designed mutants, IL-4W91S (♦) and IL-4BChelix (○), followed by CD. The denaturation process is reversible both for IL4Wt and the two mutant proteins. b Chemical denaturation profile of IL4WT (+), and the two variants, IL-4W91S (○) and IL-4BChelix (●) followed by CD. The experimental data is represented by scattered symbols and solid lines show the best fit to the experimental data assuming a two state transition model, according to equation 6. The thermodynamic parameters obtained from the fitting, together with the temperature denaturation data, are summarized in Table 4.
Figure 11B:
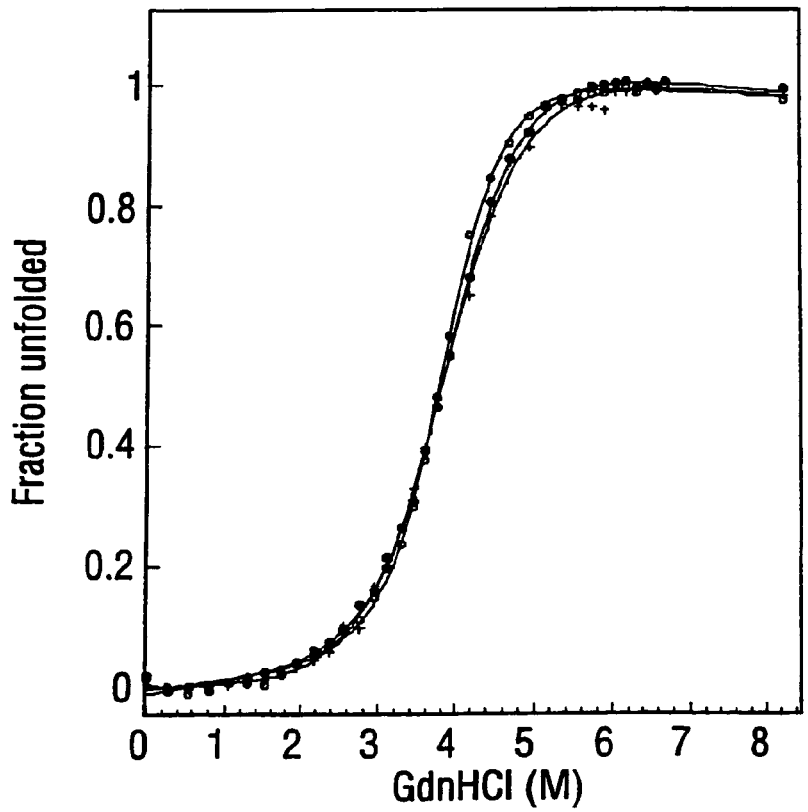

In order to investigate the effect of the designed mutations on the stability of the protein, we have carried out equilibrium thermal (FIG. 11a) and chemical denaturation studies (FIG. 11b). IL-4 is a too stable protein to be denatured by temperature in the 0 to 100° C. range. Therefore, to observe a complete unfolding transition, the thermal denaturation experiments were carried out in the presence of 2 M GdmHCl. Under these conditions, the whole transition can be observed. Interestingly, cold denaturation can be observed for the WT protein, below 20° C. At higher GdmHCl concentrations the proteins are fully denatured at high temperature, but they are not fully folded at low temperatures. As a result it is not possible to obtain accurate thermodynamic data from the generated curves, although the temperature at which half of the protein is denatured, Tm, can be determined with reasonable accuracy (Table 4).

TABLE 4

Free Energy changes for Unfolding by GdmHCl and midpoint transition Temperature. Tm. of IL-4 wild type and the stabilized mutants.

| Protein | $\Delta G^{H_2O}$ (kcal/mol) | m (Kcal/mol)/M | $[GdmGCl]_{1/2}$ (M) (° C.) | Tm |
| --- | --- | --- | --- | --- |
| IL-4 WT | 4.3 ± 0.16 | 1.1 ± 0.01 | 3.8 ± 0.12 | 62 |
| IL-4 BChelix | 4.8 ± 0.14 | 1.2 ± 0.04 | 3.9 ± 0.10 | 68 |
| IL-4 W91S | 5.7 ± 0.20 | 1.5 ± 0.05 | 3.8 ± 0.15 | 70 |

The stability of the two mutants in their oxidized form was determined and compared to the wild type protein. An unfolding free energy of 4.3 kcal/mol was obtained for IL-4WT. This value is 1.6 kcal/mol lower than that found in a previously published study (Windsor et al., 1991). However, the fitting of the data in the latter work is not accurate and the errors are not provided. A closer inspection of the data presented therein, suggests a free energy of unfolding for IL-4WT of about 4.5 kcal/mol, in agreement with our results.

Removal of solvent exposed hydrophobic residues should stabilize the target protein through the "inverse hydrophobic effect" (Pakula & Sauer, 1990). In our case, substitution of W91 by serine stabilizes the wild type protein by 1.4 kcal/mol and induces a shift of 8° C. in the Tm value. The observed stabilization arises from an increase in the steepness of the unfolding process, which is reflected in an increase in the m value. This increase in steepness might be due to the destabilization of a folding intermediate, the denatured state, or both (for a comprehensive review see Shortle D. 1996). A similar effect (increase in ΔG of 1.4 kcal/mol and increase in m value from 1.6 to 1.9) was found in the chemotactic protein, CheY, when a solvent exposed Phe residue (F14) was replaced by Asn (Muñoz et al., 1994a; Lopez-Hernandez el al. 1997). In this case, the change in slope was due to a relative destabilization of a folding intermediate, which could only be detected kinetically. We have tried to fit the equilibrium denaturation and renaturation curves of IL-4 assuming a three-state model. Like for Che Y, we could not detect any significant improvement in the fitting of the curves. Therefore, at present we cannot assign the change in m to a destabilization of an equilibrium folding intermediate present in the folding of the oxidized protein.

As far as helix stabilization is concerned, it has been shown that it will always result in an increase in protein stability and in some cases could produce thermostable proteins (Villegas el al., 1996 see chapter 2), but the increase in stability is always less than expected from the theoretical prediction. This is due to the simultaneous stabilization of the denatured state under native conditions. The mutations introduced into helix C, stabilize the protein to a less extent (0.5 kcal/mol) and induce a smaller shift (6° C.) in the Tm of IL-4WT. In this case, the stabilization effect arises from a combination of an increase in the steepness of the transition (m value), and a slight increase in the GdnHCl concentration necessary to denature half of the protein. [GdnHCl]$_{1/2}$. Although the increase in m value observed for this mutant is not large, it was consistently observed in two independent denaturation and renaturation experiments.

It is worth noting that the m values obtained in this study (table 1) are quite small for a protein of the size of IL-4 (15 kDa). This may be due to the fact that the unfolding and refolding experiments were carried out in the absence of reducing agents. Therefore, the three disulfide bridges are formed in the denature state, which might lead to the presence of some residual structure.

REFERENCES

Alber, T. (1992), Structure of the leucine zipper, *Curr. Opin. Genet. Dev.* 2, 205–210.

Amrein. K. E., Takacs, B., Stieger, M., Molnos, J., Flint, N. A. & Burn. P. (1995), Purification and characterization of recombinant human p50csk protein- tyrosine kinase from an *Escherichia coli* expression system overproducing the bacterial chaperones GroES and GroEL. *Proc Natl Acad Sci USA* 92, 1048–52.

Baker, D., Silen, J. L. & Agard, D. A. (1992). Protease pro region required for folding is a potent inhibitor of the mature enzyme. *Proteins* 12, 339–44.

Baldwin. R. L. (1996). On-pathway versus off-pathway intermediates. *Folding & Design* 1, R1–R8.

Bazan, J. F. (1990). Structural design and molecular evolution of a cytokine receptor superfamily. *Proc. Natl. Acad. Sci. USA* 87, 6934–6938.

Blum, P., Velligan, M., Lin, N., Matin, A. (1992). DnaK-mediated alterations in human growth hormone protein inclusion bodies. *Bio/technol.* 10, 301–304.

Booth, D. R., Sunde, M., Belloti, V., Robinson, C. V., Hutchinson, W. L., Fraser, P. E., Hawkins, P. N., Dobson, C. M., Radford, S., Blake, C. C. F., Pepys, M. B. (1997). Instability, unfolding and aggregation of human lysozyme variants underlying amyloid fibrillogenesis. *Nature* 385(27), 787–793.

Bowden, G., Georeiou, G. (1990). In *Recombinant DNA technology and applications* Prokop, A., Bajapi, K. R., Ho, C. (eds.), McGraw-Hill.

Braig, K., Otwinowski, Z., Hegde, R., Boisvert, D. C., Joachimiak, A., Horwich, A. L. & Sigler, P. B. (1994). The crystal structure of the bacterial chaperon in GroEL at 2.8 A [see comments]. *Nature* 371, 578–86.

Braisted. A. C., Wells, J. (1996). Minimizing a binding domain from protein A. *Proc. Natl. Acad. Sci. USA* 93, 5688–5692.

Buckel, P. (1996). Recombinant proteins for therapy. Trends in *Protein Science* 17, 450–456.

Carpino, L. A., Han, G. Y. (1972). The 9-Fluorenylmethoxycarbonyl amino-protecting group. *Journal of Organ. Chem.* 37, 3404–3409.

Chakrabartty, B. A., Baldwin, R. L. (1995). Stability of a-helices. *Adv. in Protein Chemistry* 46, 141–176.

Clackson, T., Wells, J. (1995). A hot spot of binding energy in a hormone-receptor interface. *Science* 267, 383–386.

Cole, P. A. (1996). Chaperone-assisted protein expression. *Structure* 4(3), 239–42.

Cornell, W. D., Cieplak, P., Bayly, C. I., Gould I. R., Merz Jr., K. M., Fergusson, D. M., Spellmeyer, D. C., Fox, T., Caldwell, J. W., and Kollman, P. A. (1995). A second generation force field for the simulation of proteins and nucleic acids. *JACS* 117, 5179–5197

Corrales, F. J. & Fersht, A. R. (1996). Toward a mechanism for GroEL/GroES chaperone activity: an ATPase-gated and -pulsed folding and annealing cage. *Proc Natl Acad Sci USA* 93,4509–12.

Coste, J., Le-Nguyen, D. and Castro, B. (1990). PyBOP: a new peptide coupling reagent devoid of toxic by product. *Tetrahedron Letters* 31, 205–208

Cregut, D., Serrano, L. (1999). Molecular dynamics as a tool to detect protein foldability. A mutant of domain B1 of protein G with non-native secondary structure propensities. *Protein Science* 8, 271–282

Creighton, T. E. (1997). Protein folding coupled to disulphide bond formation. *Biol Chem* 378, 731–44.

Cwirla, S. E., Balasubramanian, P., Duffin, D. J., Wagstrom, C. R., Gates, C. M., Singer, S. C., Davis, A. M., Tansik, R. L., Mattheakis, L. C., Boytos, C. M., Schatz, P. J., Baccanari, D. P., Wrighton, N. C., Barrett, R. W. & Dower, W. J. (1997). Peptide agonist of the thrombopoietin receptor as potent as the natural cytokine. *Science* 276(5319), 1696–9.

Dale, G. E., Broger, C., Langen, H., D'Arcy, A., Stüber, D. (1994). Improving protein solubility through rationally designed amino acid replacements: solubilization of the trimethoprim-resistant type S1 dihydropholate reductase. *Protein Engineering* 7, 933–939.

Dale, G. E., Schönfeld, H.-J., Langen, H., Stieger, M. (1994). Increase solubility of trimethoprim-resistant type S1 DHFR from *Staphylococcus aureus* in *Escherichia coli* cells overproducing the chaperonins GroEL and GroES. *Protein Engineering* 7, 925–931.

De Felippis, M. R., Alter, L. A. Pekar, A. H., Havel, H. A., Brems, D. N. (1993) Evidence for a self-associating intermediate during the folding of human growth hormone *Biochemistry* 32, 1555–62;

de Vos, A. M., Ultsch, M., Kossiakoff, A. A. (1992). Human Growth Hormone and Extracellular Domain of its Receptor: Crystal structure of the Complex. *Science* 255, 306–312.

Dernan, A. I., Prinz, W. A., Belin, D., Beckwith, J. (1993). Mutations that allow disulfide bond formation in the cytoplasm of *Escherichia coli. Science* 262, 1744–1747.

Doig, A. J., Williams, D. H. (1991). Is the hydrophobic effect stabilizing or destabilizing? The contribution of disulfide bonds to protein stability. *J. Mol. Biol.* 217, 389–398.

Duschl, A. (1995). An antagonist mutant of interleukin-4 fails to recruit γc into the receptor complex. *Eur. J. Biochm.* 228, 305.

Eder, J. & Fersht, A. R. (1995). Pro-sequence-assisted protein folding. *Mol Microbiol* 16, 609–14.

Eder, J., Rheinnecker, M. & Fersht, A. R. (1993). Folding of subtilisin BPN': role of the pro-sequence. *J Mol Biol* 233, 293–304.

Emmos, T. -K., Murali. R., Greene, M. (1997). Therapeutic peptides and peptidomimetics. *Current Opinion in Biotechnology* 8, 435–441.

Filimonov, V. V., Prieto, J., Mateo, P.L. & Serrano, L. (1993). Thermodynamic analysis of the chemotactic protein from *E. coli*, CheY. *Biochemistry* 32, 12906–12921.

Fink, A.L. (1998). Protein aggregation: folding aggregates, inclusion bodies and amyloid *Folding & Design* 3, R9–23.

Finkelman, F. D., Madden, K. B., Morris, S. C., Holmes, J. M., Boiani, N., Katona, I. M., Maliszewski, C. R. (1993). Anti-cytokine antibodies as carrier proteins: prolongation of in vivo effects of exogenous cytokines by injection of cytokine-anti-cytokine antibody complexes. *J. Immunol.* 151, 1235.

Furlong, J., Meighan, M., Conner, J., Murray, J. & Clements, J. B. (1992). Methods for improved protein expression using pET vectors. *Nucleic Acids Res* 20, 4668.

Georgiou, G., Valax, P. (1996). Expression of correctly folded proteins in *Escherichia coli*. *Curr. Opin. Biotechnol.* 7, 190–197.

Grunewald, S. M., Werthmann, A., Schnarr, B., Klein, C. E., Brõcker, E. B., Mohrs. M., Brombacher, F., Sebald, W., Duschl, A. (1998). An antagonist IL-4 mutant prevents type 1 allergy in the mouse; inhibition of the IL-4/IL-13 receptor system completely abrogates humoral and immmune response to allergen and development of allergic symptoms in vivo. *J. Immunol.* 160,4004–4009.

Harbury, P. B., Zhang, T., Kim, P. S., Alber, T. (1993). A switch between two-, three-, and four-stranded coiled coils in GCN4 leucine zipper mutants. *Science* 262, 1401–1407.

Hartl, F. U., Hlodan, R. & Langer, T. (1994). Molecular chaperones in protein folding: the art of avoiding sticky situations. *Trends Biochem Sci* 19, 20–5.

Heyrovska, N., Frydman, J., Hohfeld, J. & Hartl, F. U. (1998). Directionality of polypeptide transfer in the mitochondrial pathway of chaperone-mediated protein folding. *Biol Chem* 379, 301–9.

Ho, S. N., Hunt, H. D., Horton. R. M., Pullen, J. K., Pease. L. R. (1989). Site-directed mutagenesis by overlap extension using the polymerase chain reaction. *Gene* 77, 51–59.

Hockney, R. C. (1994). Recent developments in heterologous protein production in *E. coli. Trends Biotechnol.* 12, 456–463.

Jones, D. T. (1997) Progress in Protein Structure Prediction *Curr Opin Struct Biol* 7, 377–87.

Kato, K., Yamada, T., Kawahara, K., Onda, H., Asano, T., Sugino, H., Kakinuma, A. (1985). Purification and characterization of recombinant human interleukin-2 *Biochem and Biophys Res Comm* 130, 692–699.

Kella, N. K. D., Kinsella, J. E. (1985) Method for the controlled cleavage of disulfide bonds in proteins in the absence of denaturants *J. Biochem. Biophys. Methods* 11, 152–263.

Kenar, K. T., Garcia-Moreno, B., Freire, E. (1995). A calorimetric characterization of the salt dependence of the stability of the GCN4 leucin zipper. *Protein Science* 4, 1934–1938.

Kohn, W. D., Hodges, R., S. (1998). de novo design of a-helical coiled coils and bundles: models for the development of protein design principles. *Trends in Biotechnol* 16, 379–389.

Kouzarides, T., Ziff, E. (1989). Leucine zippers of fos, jun and GCN4 dictate dimerization specificity and thereby control DNA binding. *Nature* 340, 568–571.

Kruse, N., Lehrnbecher, T., Sebald, W. (1991). Site-directed mutagesis reveals the importance of disulfide bridges and aromatic residues for structure and proliferative activity of human interelukin-4. *FEBS* 286(1,2), 58–60.

Kruse, N., Shen, B-J., Arnold, S., Tony, H-P., Müller, T., Sebald, W. (1993). Two distinct functional sites of human interelukin 4 are identified by variants impaired in either receptor binding or receptor activation. *EMBO J* 21(13), 5121–5129.

Kruse, N., Tony, H-P., Sebald, W. (1992). Conversion of human IL-4 into a high affinity antagonist by a single amino acid repalcement. *EMBO Journal* 11(9), 3237–3244.

Lacroix, E., Viguera, A. R., Serrano, L. (1998). Elucidation of the folding properties of alpha-helices: local motifs, long-range electrostatics, ionic-strength dependene and prediction of NMR parameters. *J. Mol. Biol.* 284, 173–191.

Langer, T., Lu, C., Echols, H., Flanagan, J., Hayer, M. K. & Hartl, F. U. (1992). Successive action of DnaK, DnaJ and GroEL along the pathway of chaperone-mediated protein folding. *Nature* 356, 683–9.

Lawson J. E., Niu, X. D., Browning, K. S., Trong, H. L., Yang, J., Reed, L. J. 1993, Molecular cloning and expression of the catalytic subunit of bovine pyruvate dehydrogenase phosphatase and sequence similarity with protein phosphatase 2C *Biochemistry* 32, 8987–93.

Livnah, O., Stura, E. A., Johnson. D. L., Middleton, S. A., Mulcahy, L. S., Wrighton, N. C., Dover, W. J., Jollife, L. K., Wilson, I. A. (1996). Functional mimicry of a protein hormone by a peptide agonist: The EPO Receptor complex at 2.8 A. *Science* 273, 464–471.

Maliszewski, C. R., Sato, T. A., Davison, B., Jacobs, C. A., Finkelman, F. D., Fanslow, W. C. (1994). In vivo biological effects of soluble interleukin-4 receptor. *Proc. Soc. Exp. Biol. Med.* 206, 233.

Mande, S. C., Mehra, V., Bloom, B. R. & Hol. W. G. (1996). Structure of the heat shock protein chaperonin-10 of Mycobacterium leprae [see comments] [published erratum appears in Science 1996 Mar 22;271 (5256):1655]. *Science* 271. 203–7

Martin, J. & Hartl, F. U. (1994). Molecular chaperones in cellular protein folding. *Bioessays* 16, 689–92.

Matthews, D. J., Clark, P. A., Herbert, J., Morgan, G., Armitage, R. J., Kinnon. C., Minty A., Grabstein, K. H., Caput, D., Ferrara, P., Callard, R. (1995). Function of the interelukin-2 (IL-2) receptor gamma chain in biological responses of X-linked severe combined immunodeficient B cells to IL-2, IL-4, IL-13 and IL-15. *Blood* 85, 38.

Mott, H. R., Campbell, I. D. (1995). Four-helix bundle growth factors and their receptors: protein-protein interactions. *Current Opinion in Structural Biology* 5, 114–121.

Miller, T., Dieckmann, T., Sebald, W., Oschkinat, H. (1994). Aspects of receptor binding and signalling of interleukin-4 investigated by site-directed mutagenesis and NMR spectroscopy. *J. Mol. Biol.* 237, 423–436.

Muñoz, V., Lopez, E. & Serrano, L. (1994a). Kinetic characterization of the chemotactic protein from *E. coli* Che Y, Kinetic analysis of the inverse hydrophobic effect. *Biochemistry* 33, 5858–5866.

Muñoz, V., Serrano, L. (1994b). Elucidating the folding problem of helical peptides using empirical parameters. *Nat. Struc. BioL* 1, 399–409.

Muñoz, V., Serrano, L. (1994c). Elucidating the folding problem of a-helical peptides using empirical parameters, II. Helix macrodipole effects and rational modification of the helical content of natural peptides, *J. Mol. Biol.* 245, 275–296.

Muñoz, V., Serrano, L. (1994d). Elucidating the folding problem of a-helical peptides using empirical parameters III: Temperature and pH dependence, *J. Mol. Biol.* 245, 297–308.

Muñoz, V., Serrano, L. (1994e). Intrinsic secondary structure propensities of the amino acids, using statistical phi-psi matrices. Comparison with experimental scales. *Protein Struct. Funct. and Genetics* 20, 4.

Muñoz, V., Serrano, L. (1997). Development of the multiple sequence approximaton within the AGADIR model of a-helix formation:comparison with the Zimm-Bragg and Lifson-Roig Formalisms. *Biolpoly.* 41,495–509.

O'Shea, E. K., Klemm, J. D., Kim, P. S., Alber, T. (1991). X-ray structure of the GCN4 leucine zipper, a two-stranded, parallel coiled coil. *Science* 25, 539–544

Ohgushi, M. & Wada, A. (1983). 'Molten-globule state': a compact form of globular proteins with mobile sidechains. *FEBS Lett* 164(1), 214.

O'Shea E., K., Rutkowski, R., Stafford III, W. F., Kim, P. S. (1989). Preferential heterodimer formation by isolated leucin zippers from Fos and Jun. *Science* 245, 646–648.

Pace, C. N. (1986). *Methods Enymol.* 131, 226.

Pace, C. N., Bret, A., Thomson, S., Thomson, J. A. (1990). Measuring the conformational stability of a protein. In *Protein Structure—A Practical Approach.* Creighton, T. (ed.), 311–321. Oxford University Press, New York.

Pace, C., N., Vajdos, F., Fee, L., Grimsley, G., Gray, T. (1995). How to measure and predict the molar absorption coefficient of a protein. *Protein Science* 4, 2411–2423.

Pakula, A., Sauer, R. (1990). Reverse hydrophobic effects relived by amino acid substitutions at a protein surface. *Nature* 344, 363–364.

Pearlman. D. A., Case. D. A., Caldwell, J. C., Ross, W. S., Cheatham. T. E., Fergusson. D. M., Seibel, G. L., Chancra Singh, U., Weiner, P., Kollman, P. A. (1995). AMBER 4.1. UCSF, University of California, San Francisco. USA Peränen. J., Rikkonen, M.. Hyvonen. M., Kääriainen, L. (1996). T7 Vectors with a modified T7lac promoter for expression of proteins in *Escherichia coli. Analytical Biochemistry* 236, 371–373.

Përez-Përez, J., Martinez-Caja, C., Barbero, J. L., Gutierrez, J. (1995). DNAK/DNAJ supplementation improves the periplasmic prodcution of human Granulocyte-colony Stimulating Factor in *E. coli. Biochem. and Biophys. Res. Comm.* 210, 524–529.

Ramanathan, L., Ingram, R., Sullivan. L., Greenberg, R., Reim, R., Trotta, P. P., Le, H. V. (1993). Immunochemical mapping of domains in human interleukin 4 recognised by neutralizing monoclonal antibodies. *Biochemistry* 32, 3549–3556.

Redfield, C., Boyd, J., Smith, L. J., Smith, R. A. G., Dobson, C. M. (1992. Loop mobility in a four-helixbundle protein: 15 N NMR relxation measurements on human interleukin-4. *Biochemistry* 31(43), 10431–10437.

Redfield, C., Smith, L. J., Boyd, J., Lawrence, G. M. P., Edwards, R. G.. Gershater, C. J., Smith, R. A. G., Dobson C. M. (1994a). Analysis of the solution structure of human interleukin-4 determined by heteronuclear three-dimensional Nuclear Magnetic Resonance techniques. *J. Mol. Biol.* 238, 23–41.

Redfield, C., Smith, R. A. G., Dobson, C. M. (1994b). Structural characterization of a highly-ordered 'molten globule' at low pH. *Structural biology* 1(1), 23–29.

Reusch, P., Arnold, S., Heusser, C., Wagner, K., Weston, B., Sebald, W. (1994). Neutralizing monoclonal antibodies define two different functional sites in human interleukin-4. *Eur. J. Biochem.* 222, 491–499.

Rose-John, S., Heinrich, P. C. (1994). Soluble receptors for cytokines and growth factors: generation and biological function. *Biochem. J.* 300, 281–290.

Santoro, M. M., Bolen, D. W. (1988). Unfolding free energy changes determined by the linear extrapolation method. 1. Unfolding of Phenylmethanesulfonyl α-chymotrypsin using different denaturants. *Biochemistry* 27, 8063–8068.

Schellman, C. (1980). In *Protein Folding,* Jaenicke, R. (ed.), 53–61. Elsevier/North Holland, N.Y.

Scholtz, J. M., York, E. J., Stewart, J. M., Baldwin, R. L. (1991). A neutral water-soluble, alpha-helical peptide: the effect of ionic strength on the helix-coil equilibrium. *J. Am. Chem. Soc.* 113, 5102–5104.

Shen, B.-J., Hage, T., Sebald, W. (1996). Global and local determinants for the kinetics of interelukin-4/interelukin-4 receptor interaction. A biosensor study employing recombinat interleukin-4-binding protein. *Eur. J. Biochem.* 240, 252–261.

Shinde, U., Li, Y., Chatterjee, S. & Inouye, M. (1993). Folding pathway mediated by an intramolecular chaperone. *Proc Natl Acad Sci USA* 90, 6924–8.

Shortle D. (1996) The denatured state (the other half of the equation and its role in protein stability) *FABES J* 10, 27–34

Smerz-Bertling, C., Duschl, A. (1995). Both interleukin 4 and interleukin 13 induce tyrosine phosphorilation of the 140 -kDa subunit of the interleukin 4 receptor. *J. Biol. Chem.* 270, 966.

Smith, G. (1985). Filamentous Fusion Phage: novel expression vectors that display cloned antigens on the virion surface. *Science* 228, 1315–1317.

Steven, G., Williams, D. E. (1998). Cytokine Therapy: lessons learned and future challenges. *Curr. Opini. in Immunol.* 10, 501–503.

Thompson, K. S., Vinson, C. R., Freire. E. (1993). Thermodynamic characterization of the structural stability of the coiled-coil region of the bZIP transcription factor GCN4. *Biochemistry* 32(21), 5491–5496.

Tony, H.-P., Shen, B.-J., Reusch, P., Sebald, W. (1994). Design of human interleukin-4 antagonists inhibiting interelukin-4- dependent and interleukin-13-dependent responses in T-cells and B-cells with high efficiency. *Eur. J. Biochem.* 225, 659–665.

Tuffery, P., Etchebest, C., Hazout, S., Lavery, R. (1991). A new approach to the rapid determination of protein side chain conformation. *Journal of Biomolecular structure and dynamics* 8(6), 1267–1289.

Turner, R., Tjan, R. (1989). Leucine repeats and adjcent DNA binding mediate the formation of functional c-Fos-c-Jun heterodimers. *Science* 1989(243), 1689–1694 van Gunsteren, W. F., Berendsen, H. J. C. (1977). Algorithms for macromolecular dynamics and constraint dynamics. *Mol. Phys.* 34. 1311–1327

Viguera, A. R., Serrano, L. (1995). Experimetnal anlaysis of the Schellman motif. *J MoL Biol.* 251, 150–160.

Wang, Y., Shen, B-J., Sebald, W. (1997). A mixed-charged pair in human interleukin-4 dominates high-affinity interaction with the receptor a chain. *Proc. Natl. Acad Sci. USA* 94, 1657–1662.

Weigel, U., Meyer, M., Sebald, W. (1989). Mutant proteins of human interleukin 2. *Eur. J Biochem.* 180, 295–300.

Wrighton, N. C., Farrell, F. X., Chang, R., Kashyap, A. K., Barbone, F. P., Mulcahy, L. S., Johnson, D. L., Barrett, R. W., Jolliffe, L. K., Dower, W. J. (1996). Small peptides as potent mimetics of the Protein Hormone Eritropoietin. *Science* 273, 458–463.

Watrich, K. (1996). *NMR of Proteins and Nucleic Acids, Wiley,* N.Y.

Youngman, K. M., Spencer, D. B., Brems, D. N., De Felippis, M. R. (1995) kinetics analysis of the folding of human growth hormone. Influence of disulfide bridges *J Biol Chem* 270 19816–22).

Zhou, N. E., Kay, C. M., Hodges, R. S. (1993). Disulfide bond contribution to protein stability: positional effects of substitution in the core of the two-stranded alphahelical coiled-coil. *Biochemistry* 32, 3178–3187.

What is claimed is:

1. An isolated human IL-4 containing a serine residue at position 69, and the sequence Ala-Glu-Ala-Asn at positions 71–74 In the full length IL-4 amino acid sequence.

2. Human IL-4 according to claim 1, having at positions 68–95 in the full length amino acid sequence, the sequence SEQ ID-NO: 4 (ASAAEANRHKQLIRFLKRLDRNL-WGLAG).

3. A pharmaceutical composition comprising a human IL-4 according to claim 1 or a pharmaceutically acceptable salt thereof, and a pharmaceutically acceptable carrier.

4. A diagnostic kit comprising a human IL-4 according to claim 1.

* * * * *